(12) United States Patent
Lugade et al.

(10) Patent No.: US 8,188,269 B1
(45) Date of Patent: May 29, 2012

(54) FUNCTIONALIZED COMPOSITIONS FOR IMPROVED IMMOBILIZATION

(75) Inventors: Ananda G. Lugade, Austin, TX (US); Kurt D. Hoffacker, Austin, TX (US); Adam J. Jenkins, Austin, TX (US); Karri L. Michael-Ballard, Pflugerville, TX (US); Leonid Patsenker, Kharkov (UA); Ewald Terpetschnig, Austin, TX (US); Veronica D. Thomason, Austin, TX (US); Ralph McDade, Austin, TX (US)

(73) Assignee: Luminex Corporation, Austin, TX (US)

( * ) Notice: Subject to any disclaimer, the term of this patent is extended or adjusted under 35 U.S.C. 154(b) by 1052 days.

(21) Appl. No.: 12/119,203

(22) Filed: May 12, 2008

Related U.S. Application Data

(62) Division of application No. 11/621,209, filed on Jan. 9, 2007, now Pat. No. 7,385,053, which is a division of application No. 10/293,260, filed on Nov. 14, 2002, now Pat. No. 7,241,883.

(60) Provisional application No. 60/331,312, filed on Nov. 14, 2001.

(51) Int. Cl.
*C07D 201/00* (2006.01)

(52) U.S. Cl. ........... 540/532; 540/1; 540/210.17; 544/1; 544/2; 544/3; 544/83; 544/180; 544/182; 544/186; 506/15; 506/16; 506/18; 536/23.1; 536/25.3; 558/366; 977/902

(58) Field of Classification Search .................. 540/532, 540/25.3, 1
See application file for complete search history.

(56) References Cited

U.S. PATENT DOCUMENTS

| | | | |
|---|---|---|---|
| 5,414,135 | A | 5/1995 | Snow et al. |
| 5,736,330 | A | 4/1998 | Fulton |
| 5,981,180 | A | 11/1999 | Chandler et al. |
| 6,046,807 | A | 4/2000 | Chandler |
| 6,057,107 | A | 5/2000 | Fulton |
| 6,139,800 | A | 10/2000 | Chandler |
| 6,146,833 | A | 11/2000 | Milton |
| 6,268,222 | B1 | 7/2001 | Chandler et al. |
| 6,366,354 | B1 | 4/2002 | Chandler |
| 6,411,904 | B1 | 6/2002 | Chandler |
| 6,449,562 | B1 | 9/2002 | Chandler et al. |
| 6,602,692 | B1 | 8/2003 | Glusenkamp et al. |

FOREIGN PATENT DOCUMENTS

| | | |
|---|---|---|
| DE | 960534 | 3/1957 |
| EP | 0640589 | 3/1995 |
| GB | 985150 | 3/1965 |
| WO | 99/67228 | 12/1999 |
| WO | 00/23478 | 4/2000 |
| WO | 03/035672 | 5/2003 |

OTHER PUBLICATIONS

Zhang et al., "Studies on vaccines against cholera. Synthesis of neoglycoconjugates from the hexasaccharide determinant of *Vibrio cholerae* O:1, serotype Ogawa, by single point attachment or by attachment of the hapten in the form of clusters," Carbohydrate Research, vol. 321, 1999, pp. 157-167.

Chernyak et al., "Conjugating oligosaccharides to proteins by squaric acid diester chemistry: rapid monitoring of the progress of conjugation, and recovery of the unused ligand," Carbohydrate Research, vol. 330, 2001, pp. 479-486.

Blixt et al., "Enzymatic glycosylation of reducing oligosaccharides linked to a solid phase or a lipid via a cleavable squarate linker," Carbohydrate Research, vol. 319, 1999, pp. 80-91.

Tietze et al., "Squaric Acid Diethyl Ester: A New Coupling Reagent for the Formation of Drug Biopolymer Conjugates. Synthesis of Squaric Acid Ester Amides and Diamides," Chemische Berichte, vol. 124, 1991, pp. 1215-1221.

International Search Report, application No. PCT/US02/36458, mailed May 28, 2004.

The Chemistry of Synthetic Dyes, Chapter 1 entitled Reactive Dyes: Reactive Groups by E. Siegel, © 1972 by Academic Press, pp. 1-209.

Fulton et al., "Advanced multiplexed analysis with the FlowMetrix™ system," Clinical Chemistry, vol. 43, No. 9, 1997, pp. 1749-1756.

Hermanson, Bioconjugate Techniques, © Elsevier 1996, Chapters 1-9.

Hermanson, Bioconjugate Techniques, © Elsevier 1996, Chapters 10-17.

Frey et al., "Grafting Protein Ligand Monolayers onto the Surface of Microparticles for Probing the Accessibility of Cell Surface Receptors," Bioconjugate Chem., vol. 10, 1999, pp. 562-571.

Kettman et al., "Classification and Properties of 64 Multiplexed Microsphere Sets," Cytometry, vol. 33, 1998, pp. 234-243.

Valuev et al., "Chemical modification of polymers with physiologically active species using water-soluble carbodiimides," Biomaterials, vol. 19, 1998, pp. 41-43.

Renbaum et al., "Design of Polymeric Immunomicrospheres for Cell Labelling and Cell Separation," The British Polymer Journal, vol. 10, Dec. 1978, pp. 275-280.

Medvedkin et al., "p-Sulfotetrafluorophenyl Hydrophilic Active Esters of Amino Acids in Peptide Synthesis," Bioorg. Khirn., vol. 21, No. 9, 1995, pp. 684-690.

McDade et al., "True Multiplexed Analysis by Computer-Enhanced Flow Cytometry," Medical Device & Diagnostic Industry Magazine, Apr. 1997, pp. 75-82.

McHugh, Methods in Cell Biology, vol. 42, © Academic Press 1994, pp. 575-595.

Nikiforov et al., "Genetic Bit Analysis: a solid phase method for typing single nucleotide polymorphisms," Nucleic Acids Research, vol. 22, No. 20, 1994, pp. 4167-4175.

Upson, "Reactive Functional Latex Polymers," Journal of Polymer Science: Polymer Symposium, vol. 72, 1985, pp. 45-54.

(Continued)

*Primary Examiner* — Jeffrey S. Lundgren
*Assistant Examiner* — Ibrahim D Bori
(74) *Attorney, Agent, or Firm* — Fulbright & Jaworski LLP

(57) ABSTRACT

The present invention relates to improved covalent coupling of two or more entities such as biomolecules, polymer compositions, organic/inorganic molecules/materials, and the like, including their combinations, through one or more novel reactive groups attached to linker groups of 2-1000 atoms length. The present invention also contemplates the use of bifunctional bridge molecules to link two or more entities, wherein the functional groups of the bridge molecules are the novel reactive groups of the present invention.

5 Claims, 7 Drawing Sheets

OTHER PUBLICATIONS

Margel et al., "Polychloromethylstyrene Microspheres: Synthesis and Characterization," Journal of Polymer Science Part A: Polymer Chemistry, vol. 29, 1991, pp. 347-355.

Margel et al., Novel Effective Immunoadsorbents Based on Agarose-Polyaldhyde Microsphere Beads: Synthesis and Affinity Chromatography, Analytical Biochemistry, vol. 128, 1983, pp. 342-350.

Ugelstad et al., "Swelling of Oligomer-Polymer Particles, New Methods of Preparation of Emulsions and Polymer Dispersions," Advances in Colloid and Interface Science, vol. 13, 1980, pp. 101-140.

Arshady, "Microspheres for biomedical applications: preparation of reactive and labelled microspheres," Biomaterials, vol. 14, No. 1, 1993, pp. 5-15.

Gilles et al., "Stability of Water-Soluble Carbodiimides in Aqueous Solution," Analytical Biochemistry, vol. 184, 1990, pp. 244-248.

Renbaum et al., "Synthesis and Reactions of Hydrophilic Functional Microspheres for Immunological Studies," J. Macromol. Sci.-Chem., vol. A13, No. 5, 1979, pp. 603-632.

Chan et al., "Inactivation of Bovine Thrombin by Water-Soluble Carbodiimides: The Essential Caroxyl Group has a pKa of 5.51," Biochemical and Biophysical Research Communications, vol. 151, No. 2, Mar. 1988, pp. 709-716.

Office Action Mailed Dec. 21, 2005 for U.S. Appl. No. 10/293,260.

Office Action Mailed Apr. 27, 2006 for U.S. Appl. No. 10/293,260.

Notice of Allowance Mailed Sep. 27, 2006 for U.S. Appl. No. 10/293,260.

Office Action Mailed Sep. 17, 2007 for U.S. Appl. No. 11/621,209.

Notice of Allowance Mailed Jan. 29, 2008 for U.S. Appl. No. 11/621,209.

Office Action Mailed Feb. 12, 2008 for Canadian Patent Application No. 2,464,144.

FUNCTIONALIZED COMPOSITIONS FOR IMPROVED IMMOBILIZATION

1. CONTINUING DATA

The present application is a divisional from U.S. application Ser. No. 11/621,209 filed Jan. 9, 2007 which is a divisional from U.S. application Ser. No. 10/293,260 filed Nov. 14, 2002 which claims priority to U.S. Provisional Application No. 60/331,312 filed Nov. 14, 2001, all of which are incorporated herein by reference.

2. FIELD OF THE INVENTION

The present invention relates to improved covalent coupling of two or more entities such as biomolecules, polymer compositions, organic/inorganic molecules/materials, and the like, including their combinations, through one or more novel reactive groups attached to linker groups of 2-1000 atoms length.

3. BACKGROUND OF THE INVENTION

The immobilization of entities (such as enzymes, antibodies, proteins, DNA, nucleotides, PNA, carbohydrates, fatty acids, lectins, peptides, receptors, chromophores, fluorophores, chemiluminescent compounds, dendrimers, J or H aggregates, cells, bacteria, viruses, whole prokaryotic or eukaryotic organisms, membranes (synthetic or natural), fullerenes, nanotubes and the like) can be achieved by simple covalent reaction with an activated solid surface. For example, particles (e.g., micro- and nano-spheres; metal particles comprised of one or more metals with any size, shape, or composition; semiconductor particles, molecularly imprinted polymers (MIPS), magnetic particles; or dyed materials) or microtiter plates are a common solid matrix in many immobilization systems. Preparing and maintaining the active, functionalized surface is an important factor to assure immobilization of sufficient biological material for development of a sensitive assay. Current immobilization procedures of biomolecules on solid surfaces generally involve reactions of an activated amino or carboxyl group derivatized solid surface with amino- or thiol-modified biomolecules. After activation, or after introduction of a functionalized spacer, these groups offer direct attachment sites. Most of these functional groups (such as NHS esters, isothiocyanates, etc.) are prone to hydrolysis in an aqueous environment and become non-reactive (i.e., chemically inactive) in a matter of less than an hour.

Reactive or functionalized microspheres are conventionally produced via copolymerization of suitably functionalized monomers, or via post-chemical modification of pre-formed microspheres. Post-functionalization is a popular method for preparing reactive particles as earlier described by Upson (J. Polym. Sci., Polym. Symp. 1985, 72, 45).

In the last three decades the advancements in the field of affinity chromatography, solid-phase synthesis, and immobilization of bio-macromolecules, such as proteins, oligonucleotides and the like, have led to microsphere-based biomedical applications. More recent work on the production and evaluation of a variety of tailor-made particles has been reported by several groups including Margel et al., (J. Polym. Sci. 1991, A-29, 347-355; Anal. Biochem. 1981, 128, 342-350), Ugelstad et al., (Makromol. Chem. 1979, 180, 737-44; Adv. Colloid Interface Sci. 1980, 13, 102-140), and Rembaum et al. (Br. Polym. J. 1978, 10, 275-280; J. Macromol. Sci. Chem. 1979, A-13, 603-632). A review by R. Arshady, (Biomaterials, 1993, 14, 5-15) describes the synthesis and physicochemical properties of reactive and labeled microspheres.

Assays based on fluorescent microspheres for multiplexed analysis have been reported by several groups (Fulton et al., Clin. Chem. 1997, 43, 1749-56; Kettman et al., Cytometry, 1998, 33, 234-43; McDade et al., Med. Dev. Diag. Indust. 1997, 19(4), 75-82; McHugh, Methods Cell Biol. 1994, 42, 575-95; Nikiforov et al., Nucleic Acid Res. 11994, 22, 4167-75; U.S. Pat. No. 6,449,562; U.S. Pat. No. 5,981,180; U.S. Pat. No. 6,046,807; U.S. Pat. No. 6,057,107; U.S. Pat. No. 6,268,222; U.S. Pat. No. 6,366,354; U.S. Pat. No. 6,411,904; U.S. Pat. No. 5,736,330; U.S. Pat. No. 6,139,800).

Fray et al. have reported a strategy in which particles are pre-activated with hydrolysis-resistant aldehyde functional groups but low reaction yields of <8% have been observed with these microspheres (Bioconjugate Chem. 1999, 10, 562-71). Milton of Beckman Coulter, Inc. has reported a reaction between an acyl fluoride activated polymer-surface and an amino derivatized biomolecule at room temperature (U.S. Pat. No. 6,146,833; Nov. 14, 2000). The use of fluorophenyl resins in the solid phase synthesis of amides, peptides, hydroxamic acids, amines, urethanes, carbonates, sulfonamides and alpha-substituted carbonyl compounds has been published (WO 99/67228).

Medvedkin et al. have used sulfo-tetrafluorophenyl activated esters in peptide synthesis and demonstrated their reactivity combined with good stability under aqueous storage conditions (Bioorg. Khim. 1995, 21(9), 684-90). Apparently, the pre-activation of polystyrene surfaces with this reagent has not yet been reported prior to the present application.

Hoechst claimed the use of reactive vinyl sulfone (VS)-modified dyes for dyeing of cellulose and wool fibers in 1950 (DBP 960,534). A review by Siegel gives a complete account of reactive dyes based on vinyl sulfones (VS) and its protected 2-sulfatoethyl and 2-thiosulfatoethyl sulfones (E. Siegel in *The Chemistry of Synthetic Dyes* Vol. VI, (Ed. K Venkataraman); 2-108, Academic Press, 1972). Sterling Winthrop Inc, has demonstrated modification of proteins with PEG-supported vinyl sulfone (U.S. Pat. No. 5,414,135).

The most frequently used method to immobilize biomolecules (such as oligonucleotides, proteins, or carbohydrates) onto fluorescent microspheres is by activating surface carboxy groups. The activation requires excess EDC and a coupling pH of 4 to 6. The reaction involves the intermediate formation of an activated O-acylurea derivative between the carbodiimide and carboxyl functions. A subsequent nucleophilic attack by the primary nitrogen of the amino-groups of the biomolecule brings about the formation of the amide linkage with the release of the substituted urea. The optimum pH for the formation of O-acylurea is about pH 4-5. The intermediate has an extremely short half-life and rapidly undergoes hydrolysis or rearranges to give the N-acylurea adduct. The primary amino group of the nucleophile is predominantly protonated at about pH 4-5 and is thus mostly unreactive. These limitations can severely restrict coupling yields. At low pH, the nucleic acid bases undergo intensive protonation. Such type of protonation induces a DNA melting that exposes the hydrophobic core of the helix, enhancing nonspecific hydrophobic interactions with the solid matrix. Despite these drawbacks, EDC-mediated coupling currently is the major mode of covalent immobilization of biomolecules to solid surfaces (Hermanson, G. T. in *Bioconjugate Techniques*, Academic Press; N.Y. 1996; Andreas Frey et. al., *Bioconjugate Chem*. 1999, 10, 562-71; Maxime A. Gilles et. al., *Anal. Biochem.*, 1990, 184, 244-48; Vivien W. F. Chan et. al., *Biochem. Biophys. Res. Communications.*, 1988, 151(2), 709-16; Ivan L. Valuev et al., *Biomaterials*, 1998, 19, 41-43).

The citations of the various references described above and throughout this application are not to be taken as admissions that these references constitute prior art for the present invention. However, each of the cited references is incorporated in its entirety by reference in the present application.

4. SUMMARY OF THE INVENTION

The present invention is based, at least in part, upon improved methods and compositions for covalent coupling of two or more entities (B, B', etc.) such as biomolecules, polymer compositions, organic and/or inorganic molecules and/or materials, etc., through one or more "novel reactive groups" (Structures 1-6). The illustrations and examples provided herein are not intended to limit the scope of the invention in any way.

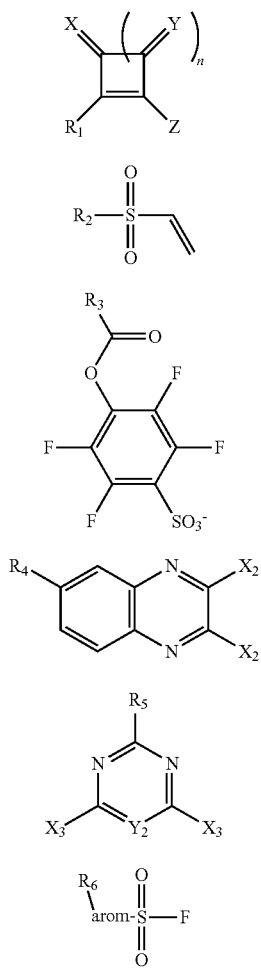

Entities B, B', etc., under the present invention comprise, but are not limited to, glass, quartz, monomer, polymer, dendrimer, MIPS, membranes, metal, clay, diatomaceous earth, particle (dyed or undyed), particle (magnetic or non-magnetic), particle (micro- or nanospheres), fullerenes, nanotubes, biomolecule, chromophore, fluorophore, chemiluminescent compound, semiconductor particles, semiconductor nanocrystals (quantum dots), J- or H— aggregates, cells, organisms, bacteria, viruses, or any combination thereof. Entities B, B', etc., can be the same or different, and can be functionalized or non-functionalized.

The novel reactive groups of the present invention are conjugated to entities B, B', etc., by way of a linker, $(L)_n$, where L is a hydrocarbon linker with n number of atoms (e.g., 2 to 1000) of H, C, O, N, Si, P and S in straight or branched chains, rings, or combinations thereof.

In some embodiments, one or more entities B, B', etc., are nucleophile-containing entities, i.e., they contain hydroxyl, amine, thiol, etc., groups, or the entities are conjugated to such groups. In such cases, attachment of the novel reactive groups may be accomplished by the chemical reaction of the electrophilic reactive group of one or more of Structures 1-6 with the nucleophilic group contained on or within the entity. Such chemical reactions include, but are not limited to, nucleophilic addition or nucleophilic-based reaction known to a person of ordinary skill in the art, substitution and/or displacement.

By way of a non-limiting example, a reaction of the present invention whereby two entities, B and B', are cross-linked via one or more of Structures 1-6. Any nucleophile- or electrophile-containing groups are termed A, A', etc., where A and/or A' are a novel reactive group, or combination thereof, discussed in the present invention and/or a nucleophile (e.g., alcohol, amine, thiol, etc.), respectively. A and A' can be the same or different novel reactive group and/or the same or different nucleophile. B and B' can either be the same and/or different entities. Several possible combinations of such elements are discussed, below.

In one embodiment, one entity B, a polymeric microsphere, is conjugated with an electrophile-containing group of one of Structures 1-6 through the group's respective linker $R_1$-$R_6$. A second entity, B', a semiconductor nanoparticle, is conjugated with a nucleophilic group at its surface. A straightforward nucleophilic substitution reaction results in the linking of B with B' by way of the linker.

In yet another embodiment of a reaction linking B and B', where A and A' are both novel reactive groups of Structures 1-6, or a combination thereof, a bifunctional linker or bridge molecule is used to covalently couple the two or more entities. In one such embodiment, the bifunctionality of the linker is nucleophilic (e.g., amine, thiol, etc.). In other words, the bridge molecule contains two or more nucleophilic groups, one of which reacts with each of A and A' such that B and B' are linked through the combined length of the linker arms of A and A' and the length of the bridge molecule.

In yet another embodiment, B and B' contain A and A', respectively, which are both nucleophiles. In this embodiment, a bifunctional linker or bridge molecule is used to couple the two or more entities whereby the bifunctionality of the linker or bridge molecule are one or more novel electrophilic reactive groups of Structures 1-6, where those groups can be the same or different novel reactive groups. The bridge molecule may or may not be constructed by joining the free ends of the linkers $R_1$-$R_6$ of the respective electrophilic reactive groups of Structures 1-6. Following the reaction of these elements, B and B' are linked via the bifunctional bridge molecule binding covalently to their respective nucleophilic groups. In another version of this embodiment, if A and A' are both nucleophiles, then a bifunctional linker or bridge molecule is used to couple the two or more entities wherein C and/or C' are a functional group or groups (e.g., NHS ester, isothiocyanate, sulfonyl chloride, etc.) known to react with nucleophiles A and A'. C and C' can be the same or different functional groups which are attached to the linker or bridge molecule by way of one or more (n) novel electrophilic reactive groups of Structures 1-6 where n is the number of novel electrophilic reactive groups.

In particular, the present invention is directed toward novel conjugated compositions comprising one or more, in any combination, of Structures 1-6:

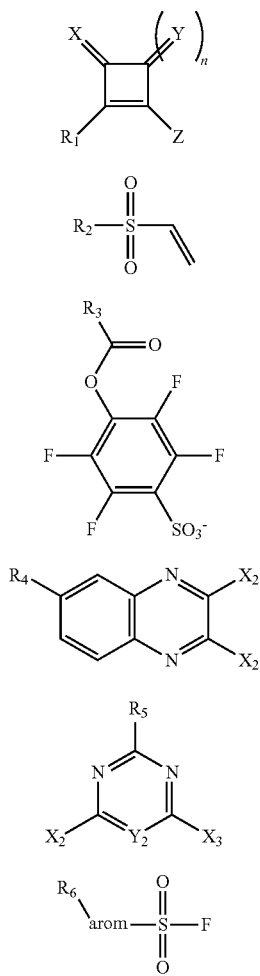

wherein:
n is 0, 1, 2, or 3;
X and Y are oxygen and/or sulfur in any combination;
$X_2$ and $X_3$ are one or more halogens, preferably chlorine or fluorine;
$Y_2$ is nitrogen or carbon;
arom is a substituted or unsubstituted phenyl, naphthyl or other polycyclic aromatic ring structure;
Z is a halide, preferably chloride or fluoride, 2,3,5,6-tetrafluoro-4-sulfo-phenoxide, N-hydroxysuccinimide or other electrophilic (nucleofugal) group; and
$R_1$-$R_6$ are hydrocarbon linker groups containing from 2-1000 atoms, optionally containing one or more halogen or heteroatoms selected from the group consisting of O, N, Si, P and S; in straight or branched chains, rings, or combinations thereof; and
wherein the one or more, in any combination, of Structures 1-6 are connected through their respective linker groups, $R_1$-$R_6$, to at least one entity B, wherein B is:
a 2-D film or substrate;
a micro- or nano-particle of any size or shape composed of organic polymer, MIPS, glass, metal, clay, resin, diatomaceous earth, zeolite, inorganic crystal, semiconductor particle, semiconductor nanocrystal, magnetic particle, fullerene, nanotube, or any combination thereof;
an enzyme, antibody, protein, DNA, RNA, nucleotide, PNA, carbohydrate, fatty acid, lectin, peptide, receptor, dendrimer, cell, bacteria, virus, whole prokaryotic or eukaryotic organism, synthetic or natural membrane, biotin, hapten, organic monomer or polymer, or any combination thereof;
a chromophore, fluorophore, bio- or chemi-luminescent compound, J or H aggregate;
one or more of Structures 1-6 connected through their respective linker groups $R_1$-$R_6$; or any combination thereof.

In yet another further embodiment, the present invention is directed to novel compositions as described above wherein $R_1$-$R_6$ contain 2-100 atoms, or more preferably wherein $R_1$-$R_6$ contain 2-10 atoms.

The present invention also encompasses compositions comprising the Structures 1-6 noted above, wherein $R_1$-$R_6$ comprise hydrocarbon linker groups containing, optionally, one or more halogen or heteroatoms selected from the group consisting of O, N, Si, P and S; in straight or branched chains, rings, or combinations thereof containing from 2-1000 atoms, preferably 2-100 atoms, or more preferably wherein $R_1$-$R_6$ contain 2-10 atoms.

The present invention also is directed toward compositions as described above wherein B is a polymeric microsphere or nanosphere. Even more preferred is an embodiment wherein the polymeric microsphere further comprises polystyrene/divinyl benzene and/or carboxyl functional groups at least on its surface, and even more preferred is an embodiment wherein the microsphere further comprises one or more fluorescent dyes in distinguishable ratios.

As noted above, the present invention relates, in a preferred embodiment, to functionalized microspheres. A series of reactive functional groups has been evaluated on polystyrene-based microspheres for their ability to immobilize biomolecules, which biomolecules comprise prokaryotic or eukaryotic cells, transgenic cells, organisms, bacteria, viruses, plasmids, expression vectors, enzymes, proteins, fusion proteins, antibodies, chimeric antibodies, DNA, RNA, PNA, fatty acids, lectins, peptides, and receptors, or any combination thereof. Activated oxocarbon acids (e.g., mono-fluoro squaric acid (MFS)), tetra-fluoro-sulfophenyl ester (TFS), vinyl sulfone (VS), dihaloquinoxaline, sulfonyl fluoride, cyanuric acid halide and halopyrimidine show improved performance for immobilizing biomolecules as they (a) spontaneously react with nucleophilic groups of biomolecules, (b) show substantially improved stability in aqueous media, (c) form stable conjugates with biomolecules, (d) require no additional activating reagents and (e) may provide more specific conjugation (i.e., reduced nonspecific interaction/binding with solid substrates) thus protecting the integrity of the biomolecule.

In yet another embodiment, a novel reactive group can be attached first to a biomolecule and then coupled to a solid support containing nucleophilic groups. Also disclosed are new linker systems aimed at improving the coupling yields of biomolecules to solid surfaces.

In particular, the present invention is directed toward a method for coupling two or more entities together by providing one or more conjugate compositions as described above having one or more, in any combination, of Structures 1-6 connected through their respective linker groups, $R_1$-$R_6$, to at least one entity B; providing one or more nucleophile-containing entities comprised of:

a 2-D film or substrate;

a micro- or nano-particle of any size or shape, composed of organic polymer, MIPS, glass, metal, clay, resin, diatomaceous earth, zeolite, inorganic crystal (including semiconductors, semiconductor nanocrystals, and magnetic particles), fullerene, nanotube or any combination thereof;

an enzyme, antibody, protein, DNA, RNA, nucleotide, PNA, carbohydrate, fatty acid, lectin, peptide, receptor, chromophore, fluorophore, bio- or chemi-luminescent compound, J or H aggregate, cell, bacteria, virus, whole prokaryotic or eukaryotic organism, synthetic or natural membrane, biotin, hapten, organic monomer or polymer, or dendrimer, or any combination thereof; and reacting the one or more conjugate compositions with the one or more nucleophile containing entities to produce at least one entity B linked through one or more linker arms of Structures 1-6 to said one or more nucleophile-containing entities.

In another embodiment, the present invention encompasses a method for the synthesis of compositions noted above wherein the one or more, in any combination, of Structures 1-6 are conjugated to the entity B before the fabrication of the entity B; during the fabrication of the entity B; or after the fabrication of entity B.

Another preferred embodiment of the present invention is directed toward a method of crosslinking one or more nucleophile-containing entities comprising reacting a composition of Structure 1, as described above, wherein:

(a) n is 0, 1, 2, or 3;
(b) X and Y are oxygen and/or sulfur in any combination;
(c) Z and $R_1$ are halogen (including chloride and fluoride); 2,3,5,6-tetrafluoro-4-sulfo-phenoxide; N-hydroxysuccinimide; and similar nucleofugal groups or any combination thereof;

with one or more nucleophile-containing entities, comprised of:

a 2-D film or substrate;

a micro- or nano-particle of any size or shape, composed of organic polymer, MIPS, glass, metal, clay, resin, diatomaceous earth, zeolite, inorganic crystal (including semiconductors, semiconductor nanocrystals, and magnetic particles), fullerene, nanotube or any combination thereof;

an enzyme, antibody, protein, DNA, RNA, nucleotide, PNA, carbohydrate, fatty acid, lectin, peptide, receptor, chromophore, fluorophore, bio- or chemi-luminescent compound, J or H aggregate, cell, bacteria, virus, whole prokaryotic or eukaryotic organism, synthetic or natural membrane, biotin, hapten, organic monomer or polymer, or dendrimer or any combination thereof;

to provide one or more crosslinked nucleophile-containing entities.

In yet an even further embodiment, the present invention is directed toward the use of Structures 1-6 in the creation of bridge molecules for linking two or more entities together, or compositions comprising one or more of Structures 1-6 as bridge molecules. Various embodiments of the present invention include multifunctional bridge molecules of two or more of Structures 1-6 joined through their respective linker groups $R_1$-$R_6$, in an end-to-end fashion, in a branched chain, or in dendritic fashion. Such bridge molecules may be used to link together covalently two or more entities having nucleophilic groups by straightforward chemical reactions such as nucleophilic addition or substitution or any other applicable chemical reaction known to a person of ordinary skill in the art.

In yet another variation of this invention, a multifunctional bridge molecule is provided wherein the functional groups are one of more of Structures 1-6 and one or more nucleophilic groups. Such bridge molecules may be used to link together covalently one or more entities having nucleophilic groups with one or more entities conjugated to one or more of Structures 1-6 by straightforward chemical reactions such as nucleophilic addition or substitution, wherein the entity(ies) having nucleophilic groups react with the bridge group functionality(ies) of Structures 1-6, and the entity(ies) having reactive groups of Structures 1-6 react with the nucleophilic bridge group functionality(ies) to yield two or more entities linked together.

Compositions of such multifunctional bridge groups are also envisioned. A bridge group composition is envisioned wherein one or more of Structures 1-6, in any combination, are conjugated by their respective linker groups $R_1$-$R_6$ to one or more nucleophilic groups, wherein if two or more of Structure 1-6 are joined together, they are joined together through their respective linker groups $R_1$-$R_6$, wherein the joining is one or more of end-to-end, branched, or dendritic, in any combination.

5. BRIEF DESCRIPTION OF THE FIGURES

Figure 7:
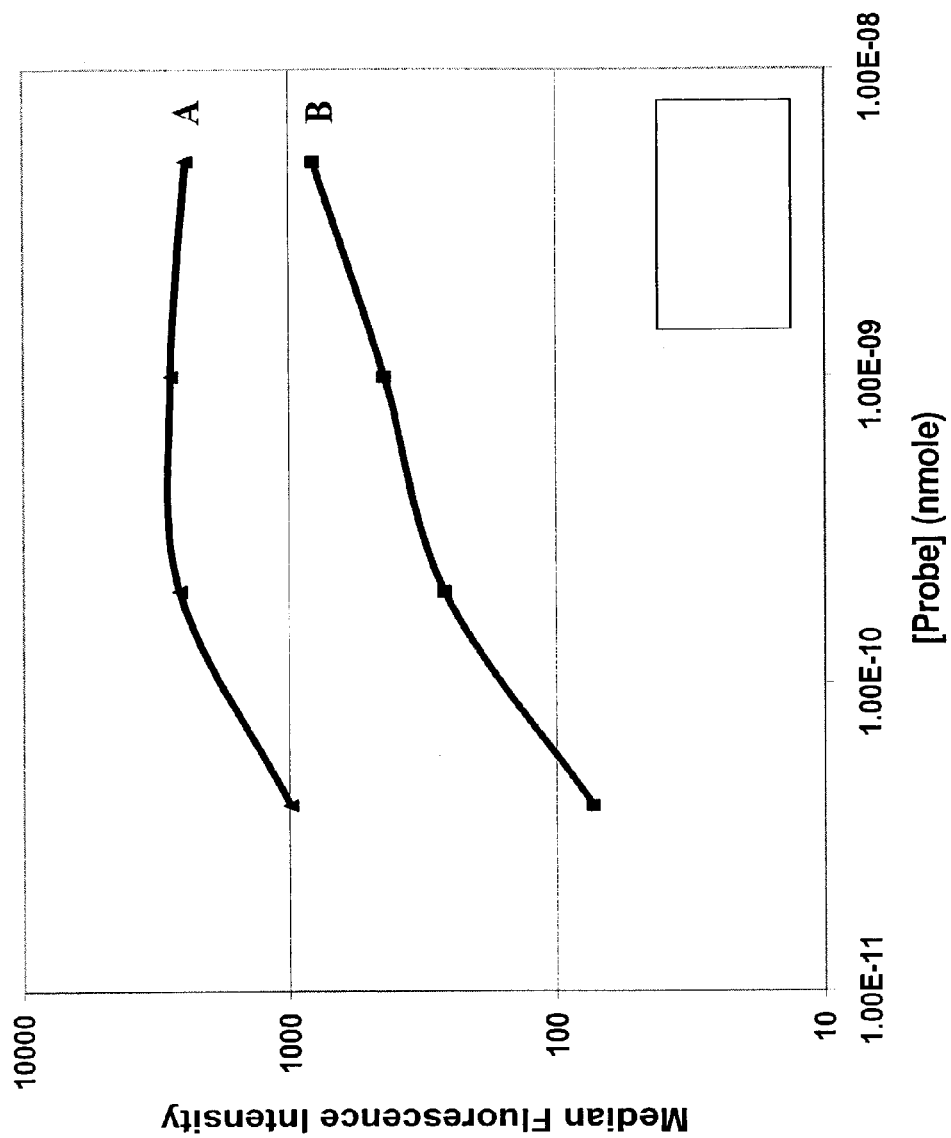

FIG. 7 shows a coupling titration of an amino-functionalized DNA probe on (A) COOH-functionalized microspheres (EDC-mediated reaction) vs. (B) mono-fluoro squaric acid (MFS)-functionalized microspheres (spontaneous reaction) methods. Both coupling titrations were performed at 25° C. The DNA compliment target concentration for the assay was 20 fmoles at a hybridization temperature of 55° C. The COOH-EDC method (A) yields a non-linear response to the amount of probe coupled to the microspheres. The mono-fluoro squaric acid-functionalized microsphere's probe titration (B) is more linear. These results are reproducible and may be the result of a more specific coupling. Note: 25° C. is not an optimal coupling temperature for the mono-fluoro squaric acid-functionalized microspheres. Signal is expected to improve with optimization of all parameters.

6. DETAILED DESCRIPTION OF THE PREFERRED EMBODIMENTS

6.1 Functional Groups

Because of the shortcomings of current coupling methods—lack of stability or inability to spontaneously react with biomolecules in aqueous media or both—the inventors decided to introduce hydrolysis-resistant, ready to use, pre-activated microspheres, for the immobilization of biomolecules. Table 1 is a partial, non-limiting, list of such novel reactive microspheres.

Sulfonyl fluorides are known to be more stable in an aqueous environment than sulfonyl chlorides (Table 1, 1a-1d) and the aromatic versions are more stable as compared to their aliphatic counter parts. Several routes starting either from acids or acid chlorides were used to synthesize sulfonyl fluorides (Table 1, 2a-2e) on the surface of polystyrene microspheres.

The cyclic oxo-carbon acids (deltic, squaric, croconic and rhodizonic) have two acid equivalents and 1-4 carbonyl groups in a ring. The inventors have used one of the acid equivalents to connect the ring to one of our linker molecules and activated the other to a reactive derivative. Several routes to synthesize squaric acid derivatized microspheres are provided in Table 1 (3a-3e). The resulting activated beads are very reactive with amine containing molecules and can be stored on a long term basis if kept dry. This class of reactive group can also be used as a replacement for NHS esters and the like to activate dyes and biomolecules.

Cyanuric fluoride can react with up to three equivalents of amine, replacing the fluorine atoms with the nitrogen atoms of the amines. The inventors have isolated microspheres in which cyanuric fluoride was reacted with one equivalent of an amine linker, which was attached to a microsphere (Table 1, 4). The second and third fluorine are still available for reaction with bio-molecules. Related molecules such as cyanuric chloride, 2,4,6-trichloro pyrimidine or 2,4,6-trifluoropyrimidine are used similarly.

Vinyl sulfone (VS) microspheres were generated by reacting divinyl sulfone with microspheres containing hydroxy, amino or thiol groups (Table 1, 5a-5b). The remaining vinyl moiety is available for reaction with both thiols and amines. This group is less susceptible to hydrolysis, but requires a basic pH for reaction with amines. The vinyl sulfone (VS) group can be protected from oxidation during long term storage by reacting it with sodium thiosulfate as in Table 1, 5c. The vinyl moiety is regenerated at about pH 9-10.

Perfluorinated phenols have been developed as hydrolysis resistant replacements for N-hydroxysuccinimide for conventional coupling chemistries. The inventors reacted tetrafluoro-phenolsulfonic acid with carboxylic acid groups directly on the surface of microspheres (Table 1, 6) or on the end of a linker molecule. Fluorine atoms provide the moiety with a good leaving group and the sulfonic acid maintains the charge on the surface of the microsphere, which is needed to disperse it in water.

6.2. Linkers

The overall performance of a functionalized microsphere is controlled by several parameters—microsphere charge, density of cross-linking, location, accessibility and chemical stability of functional groups, length, charge and nature of the linker group.

Linkers play an important role in bioconjugations. They are selected based not only on their length, but their chemical nature. The overall nature of the linker is known to govern the overall hydrophilicity or hydrophobicity of the reagent environment. It is well understood that extended linkers can reduce the steric interferences between the analyte and the solid matrix.

Several different classes of linkers could be used to connect the above mentioned functional groups to microspheres. Examples of these linkers are shown in Table 2.

Ethylene glycol based linkers (Table 2, 1-3) are surface modifiers which are known for improving the stability of hydrophilic surfaces. Additional stability is ensured by replacing $CH_2$ with $CF_2$. Straight chain polymethylenes (Table 2, 4) are other linkers that may be used to connect the above mentioned functional groups to microspheres.

Diamines and hydrazides are known to provide hydrophobic surfaces (Table 2, 5-8). Polyethylenimines (Table 2, 9) exhibit a 'proton sponge' effect, which can be used to control the surface charge of the microsphere. Polyamides and polysulfonamides (Table 2, 10-13) contain acidic protons with a pKa of about 1-2. These linkers, therefore, provide polyanions at physiological pH and hence provide long storage stability. Dendrimers or highly branched linkers (Table 2, 14) are known to adopt to well defined morphologies and provide a kind of encapsulation to the reactive groups and hence protect them from hydrolysis. DTPA (diethylene triamine pentaacetic acid) linkers (Table 2, 1S) provide multiple carboxylates. These type of linkers are known to form stable metal complexes. Polyacrylic acid and polylysine chains (Table 2, 16-17) can be introduced to improve the degree of immobilization.

6.3. Examples of Specific Application

The following are examples of specific applications of the present invention. These examples are not intended to limit the scope of the invention in any way.

6.3.1 Example

This example relates to, but is not limited to, the use of functionalized, or pre-activated, microspheres for covalent immobilization of biomolecules.
  (a) A solid support comprised of a polymeric microsphere, preferably polystyrene/divinyl-benzene, containing carboxyl functional groups at least on its surface.
  (b) The solid support (a) where the solid support contains one or more fluorescent dyes in distinguishable ratios.
  (c) Solid support (b) where at least surface carboxyl groups have been modified with a 4,7,10-trioxa-1,13-tridecanediamine linker.
  (d) Solid support (c) where the linker has been modified and/or contains the novel reactive group mono-fluoro squaric acid (MFS).
  (e) A biomolecule, specifically an oligonucleotide probe, containing a primary amine terminus.
  (f) Spontaneous, covalent coupling of solid support (d) and biomolecule (e) to form a stable, covalent bond.
  (g) Use of the biomolecule-coupled solid support (f) in a single or multiplexed DNA assay.

6.3.2 Example

This example relates to, but is not limited to, the use of functionalized, or pre-activated, microspheres for covalent immobilization of biomolecules.
  (a) A solid support comprised of a polymeric microsphere, preferably polystyrene/divinyl-benzene, containing carboxyl functional groups at least on its surface.
  (b) The solid support (a) where the solid support contains one or more fluorescent dyes in distinguishable ratios.
  (c) Solid support (b) where at least surface carboxyl groups have been modified with a cystamine linker.
  (d) Solid support (c) where the linker has been modified and/or contains the novel vinyl sulfone (VS) reactive group.

(e) A biomolecule, specifically an antibody, containing a primary amine or thiol.
(f) Spontaneous, covalent coupling of solid support (d) and biomolecule (e) to form a stable, covalent bond.
(g) Use of the biomolecule-coupled solid support (f) in a single or multiplexed immunoassay.

6.3.3 Example

This example relates to, but is not limited to, the use of functionalized, or pre-activated, microspheres for covalent immobilization of biomolecules.
(a) A solid support comprised of a polymeric microsphere, preferably polystyrene/divinyl-benzene, containing carboxyl functional groups at least on its surface.
(b) The solid support (a) where the solid support contains one or more fluorescent dyes in distinguishable ratios.
(c) Solid support (b) where the carboxyl groups have been modified to contain the novel tetra-fluoro-sulfophenyl ester (TFS) reactive group.
(d) A biomolecule, specifically an antigen, containing a primary amine.
(e) Spontaneous, covalent coupling of solid support (c) and biomolecule (d) to form a stable, covalent bond.
(f) Use of the biomolecule-coupled solid support (e) in a single or multiplexed immunoassay.

6.3.4 Example

This example relates to, but is not limited to, the use of a solid surface for covalent immobilization of functionalized, or pre-activated biomolecules.
(a) A two-dimensional solid support comprised of quartz, and containing hydroxyl functional groups at least on its surface.
(b) Solid support (a) where at least surface hydroxyl groups have been modified with aminopropyl-triethoxy silane, an amino-terminated silane linker.
(c) A biomolecule, specifically an oligonucleotide, where the terminus has been modified to contain the novel reactive group mono-fluoro squaric acid (MFS).
(d) Spontaneous, covalent coupling of solid support (b) and biomolecule (c) to form a stable, covalent bond.
(e) Use of the biomolecule-coupled solid support (d) in a single or multiplexed DNA assay.

6.3.5 Example

This example relates to, but is not limited to, the use of functionalized, or pre-activated, microspheres for covalent immobilization of semi-conductor nanoparticles.
(a) A solid support comprised of a polymeric microsphere, preferably polystyrene/divinyl-benzene, containing carboxyl functional groups at least on its surface.
(b) Solid support (a) where the carboxyl groups have been modified to contain the novel vinyl sulfone (VS) reactive group.
(c) One or more semi-conductor nanoparticles having one or more distinguishable fluorescence emissions or wavelengths.
(d) Semi-conductor nanoparticles (c) having at least thiol functional groups at least on the surface of the particles.
(e) Spontaneous, covalent coupling of solid support (b) and semi-conductor nanoparticles (d) to form a stable, covalent bond.
(f) Use of the semi-conductor nanoparticles-coupled solid support (e) for decoding in a single multiplexed assay.

6.3.6 Example

This example relates to, but is not limited to, the covalent coupling of functionalized, or pre-activated, microspheres to functionalized, or pre-activated nanospheres using a linker or bridge between the two particles.
(a) A solid support comprised of a polymeric microsphere, preferably polystyrene/divinyl-benzene, containing carboxyl functional groups at least on its surface.
(b) Solid support (a) where the carboxyl groups have been modified to contain the novel mono-fluoro squaric acid (MFS) reactive group.
(c) Solid support (b) where the novel mono-fluoro squaric acid (MFS) reactive group has been modified with the bifunctional linker 4,7,10-trioxa-1,13-tridecanediamine.
(d) A second solid support comprised of polymeric nanospheres, preferably polystyrene/divinyl-benzene, containing carboxyl functional groups at least on its surface.
(e) Solid support (d) where the carboxyl groups have been modified to contain the novel mono-fluoro squaric acid (MFS) reactive group.
(f) Solid support (e) having one or more fluorescent dyes in distinguishable ratios.
(g) Spontaneous, covalent coupling of microsphere solid support (c) and nanosphere solid support (f) to form a stable, covalent bond.
(h) Use of the nanosphere-coupled microsphere solid support (g) for decoding in a single or multiplexed assay.

6.3.7 Example

This example relates to, but is not limited to, the use of functionalized, or pre-activated, microspheres for covalent immobilization of dendrimers.
(a) A solid support comprised of a polymeric microsphere, preferably polystyrene/divinyl-benzene, containing carboxyl functional groups at least on its surface.
(b) The solid support (a) where the solid support contains one or more fluorescent dyes in distinguishable ratios.
(c) Solid support (b) where the carboxyl groups have been modified to contain the novel tetra-fluoro-sulfophenyl ester (TFS) reactive group.
(d) A dendrimer containing primary amine functional groups.
(e) Spontaneous, covalent coupling of solid support (c) and dendrimer (d) to form a stable, covalent bond.
(f) Modification of the dendrimer-coupled solid support (e) with a bifunctional linker containing the novel reactive group mono-fluoro squaric acid (MFS) on both termini of the linker.
(g) A biomolecule, specifically an antibody, containing a primary amine.
(h) Spontaneous, covalent coupling of solid support (f) and biomolecule (g) to form a stable, covalent bond.
(i) Use of the biomolecule-coupled solid support (h) in a single or multiplexed immunoassay.

6.3.8 Example

This example relates to, but is not limited to, the covalent coupling of biomolecules to microspheres via a novel linker.

(a) A solid support comprised of a polymeric microsphere, preferably polystyrene/divinyl-benzene, containing carboxyl functional groups at least on its surface.
(b) The solid support (a) where the solid support contains one or more fluorescent dyes in distinguishable ratios.
(c) Solid support (b) where at least surface carboxyl groups have been modified with a novel bifunctional amine termini linker containing a least one or more squaric acid functional groups within the linker chain.
(d) A biomolecule, specifically an oligonucleotide probe, containing the novel tetra-fluoro-sulfophenyl ester (TFS) reactive group at one terminus.
(e) Spontaneous, covalent coupling of solid support (c) and biomolecule (d) to form a stable, covalent bond.
(f) Use of the biomolecule-coupled solid support (e) in a nucleic acid-based assay, wherein said assay comprises DNA, RNA, PNA, etc.

6.3.9 Example

This example relates to, but is not limited to, the covalent labeling of a biomolecule with a functionalized, or pre-activated fluorophore.
(a) A fluorophore functionalized, modified and/or synthesized to contain the novel reactive group mono-fluoro squaric acid (MFS).
(b) A biomolecule, specifically avidin, streptavidin, neutraavidin and the like containing primary amines.
(c) Spontaneous, covalent labeling of biomolecule (b) and the pre-activated fluorophore (a) to form a stable, covalent bond.
(d) A solid support comprised of a polymeric microsphere, preferably polystyrene/divinyl-benzene, containing biotin functional groups at least on its surface.
(e) The solid support (d) where the solid support contains one or more fluorescent dyes in distinguishable ratios.
(g) Use of the solid support (e) in a single or multiplexed assay where the fluorophore-labeled biomolecule (c) is used as a reporter molecule.

6.3.10 Example

This example relates to, but is not limited to, the use of functionalized, or pre-activated, biomolecules for the covalent immobilization onto a solid surface.
(a) A solid support comprised of one or more metals.
(b) The solid support (a) where the solid support has been modified with a self-assembled monolayer (SAM) to contain thiol functional groups.
(c) A biomolecule, specifically an oligonucleotide, modified and/or synthesized to contain the novel reactive group vinyl sulfone (VS) at one terminus.
(d) Spontaneous, covalent coupling of solid support (b) and biomolecule (c) to form a stable, covalent bond.
(e) Use of the biomolecule-coupled solid support (d) in a single or multiplexed nucleic acid-based assay, wherein said assay comprises DNA, RNA, PNA, etc.

6.3.11 Example

This example relates to, but is not limited to, the use of functionalized, or pre-activated, particles for the covalent immobilization of fluorophores.
(a) Solid support particles comprised of one or more metals.
(b) The solid support (a) where the solid support has been modified to contain the novel functional group mono-fluoro squaric acid (MFS).
(c) J- or H— aggregate fluorophores containing amines and a quencher molecule.
(d) Spontaneous, covalent coupling of solid support (b) and fluorophore (c) to form a stable, covalent bond.
(e) Use of the fluorophore-labeled particles (d) as a reporter in a single or multiplexed assay.

7.0 EXAMPLES OF SYNTHETIC PROCEDURES FOR PREPARING THE NOVEL REACTIVE GROUPS

Aspects of the invention include materials and procedures for preparing compositions, conjugates and/or mixtures involving polymer particles, various linkers and functional groups. These linkers and functional groups are described as follows: (7.0) synthetic procedures of surface functional groups and spacers, (7.1) evaluation of novel reactive groups, (7.2) examples of coupling procedures. Such descriptions provided herein are not intended to limit the present invention in any way.

7.0.1 Sulfonyl Chloride

The following describes a method for the preparation of an activated surface capable of immobilizing a biomolecule in accordance with the present invention. In particular, the following example describes a method for activating carboxylated polystyrene microspheres with sulfonyl chloride groups.

100 µL (approximately 11 million microspheres) of a carboxylated polystyrene microsphere solution (5.5 µm) was washed once with 250 µL of DI water, three times with 250 µL of methanol, and three times with 250 µL of benzene using centrifugation at 13,400×g for 1 minute to pellet and 20 seconds of sonication to resuspend the microspheres. Finally they were suspended in 250 µL of benzene, 50 µL of thionyl chloride was added and the microspheres were heated at 40° C. for 2 hours. Then the microspheres were washed two times with 250 µL of benzene and dried under reduced pressure (<5 torr) for 2 hours. They were suspended in a solution of potassium 7-amino-1,3-disulfonylnaphthalene in 200 µL of pyridine and kept at room temperature for 4 hours. Then they were washed two times with 250 µL of pyridine, four times with 250 µL of DI water, two times with 250 µL of methanol, and two times with 250 µL of benzene and suspended in a solution of 50 µL thionyl chloride and 25 µL of dimethylformamide (DMF) in 250 µL of benzene and kept at room temperature for 20 minutes and at 40° C. for one hour. Afterwards the reactive microspheres were washed once with 250 µL of benzene and three times with 250 µL of acetonitrile and stored in acetonitrile until used. The just described procedure is graphically described in Entry 1c of Table 1.

7.0.2 Sulfonyl Fluoride

The following describes a method for the preparation of an activated surface capable of immobilizing a biomolecule in accordance with the present invention. In particular, the following example describes a method for activating carboxylated polystyrene microspheres with sulfonyl fluoride groups.

300 µL (32 million microspheres) of a carboxylated polystyrene microsphere solution (5.5 µm) was washed two times with 500 µL of DI water, two times with 500 µL of methanol, and two times with 500 µL of benzene using centrifugation at 13,400×g for 1 minute to pellet the microspheres and 20 seconds of sonication to resuspend the microspheres. The microspheres were then suspended in a solution of 50 μL thionyl chloride in 250 μL of benzene and kept at 40° C. for 2 hours. Then they were washed three times with 500 μL of benzene and two times with 500 μL of acetonitrile and afterwards suspended in a solution of 12 mg of potassium 7-amino-1,3-disulfonylnaphthalene in 500 μL of acetonitrile and placed in a shaker at room temperature. After 14 hours the microspheres were washed two times with 500 μL of acetonitrile. The microspheres were suspended in a solution of acetonitrile containing 15 μL of cyanuric fluoride and 20 μL of pyridine and kept at −15° C. for 14 hours and afterwards washed three times with 500 μL of acetonitrile. The microspheres were suspended and stored in 1 mL of acetonitrile. The just described procedure is graphically described in Entry 2b of Table 1.

7.0.3 Mono-Fluoro Squaric Acid (MFS)

The following describes a method for the preparation of an activated surface capable of immobilizing a biomolecule in accordance with the present invention. In particular, the following example describes a method for activating carboxylated polystyrene microspheres with mono-fluoro squaric acid groups using adipic acid dihydrazide as a linker.

300 μL (32 million microspheres) of a carboxylated polystyrene microsphere solution (5.5 μm) was washed three times with 500 μL of a solution containing 0.01% Tween20 and 0.1 M MES buffer, pH 6.0 using centrifugation at 13,400×g for 1 minute to pellet the microspheres and 20 seconds of sonication to resuspend the microspheres. The microspheres were then suspended in 500 μL of a solution containing 32 mg/mL of ADH (adipic acid dihydrazide) and 2 g/mL of EDC, 0.01% Tween20, and 0.1 M MES buffer, pH 6.0 and placed on a rotating mixer for 2 hours protected from light. The microspheres were washed three times with 500 μL of water, three times with 500 μL of methanol, and three times with 500 μL of benzene. The microspheres were then suspended in 500 μL of benzene and 14, of dibutoxy cyclobutene dione was added. After shaking on a thermal shaker for 14 hours at 25° C., the microspheres were washed three times with 500 μL of benzene, three times with 500 μL of methanol, and three times with 500 μL of DI water. To the microspheres was added 5004 of a 1 M solution of sodium hydroxide. The microspheres were then placed in a thermal shaker for 2 hours at 60° C. Then they were washed with 500 μL of methanol to recover the microspheres. The microspheres were then washed with 500 μL of a 2 M solution of hydrochloric acid. Methanol was added to recover the microspheres. The microspheres were then washed three times with 500 μL of methanol and three times with 500 μL of acetonitrile. The microspheres were then suspended in 500 μL of acetonitrile. A solution of 15 μL of cyanuric fluoride and 20 μL of pyridine was added and then the microspheres were stored at −15° C. for 14 hours. The microspheres were then washed three times with 500 μL of acetonitrile. The microspheres were suspended and stored in 1 mL of acetonitrile. The just described procedure is graphically described in Entry 3c of Table 1.

7.0.4 Cyanuric Fluoride

The following describes a method for the preparation of an activated surface capable of immobilizing a biomolecule in accordance with the present invention. In particular, the following example describes a method for activating carboxylated polystyrene microspheres with cyanuric fluoride using 1,6-diaminohexane as a linker.

300 μL (32 million microspheres) of carboxylated polystyrene microsphere solution (5.5 μm) was washed three times with 500 μL of a solution containing 0.01% Tween20 and 0.1 M MES buffer, pH 6.0 using centrifugation at 13,400×g for 1 minute to pellet the microspheres and 20 seconds of sonication to resuspend the microspheres. Afterwards they were suspended in 500 μL of a solution containing 32 mg/mL of 1,6-diaminohexane and 2 g/mL of EDC, 0.01% Tween20, and 0.1 M MES buffer, pH 6.0 and placed on a rotating mixer for 2 hours protected from light. Subsequently the microspheres were washed three times with 500 μL of water, three times with 500 μL of methanol, and three times with 500 μL of acetonitrile. The microspheres were then suspended in a solution containing 500 μL of acetonitrile, 20 μL of trimethyl amine and 15 μL of cyanuric fluoride and was set for 14 hours at −15° C. Finally they were washed three times with acetonitrile. The microspheres were suspended and stored in 1 mL of acetonitrile. The just described procedure is graphically described in Entry 4 of Table 1.

7.0.5 Vinyl Sulfone (VS)

The following describes a method for the preparation of an activated surface capable of immobilizing a biomolecule in accordance with the present invention. In particular, the following example describes a method for activating carboxylated polystyrene microspheres with vinyl sulfone (VS) using 2-aminoethanethiol as a linker.

300 μL (32 million microspheres) of a carboxylated polystyrene microsphere solution (5.5 μm) was washed three times with 500 μL of 0.1 M MES buffer, pH 6.0 including 0.01% Tween 20 using centrifugation at 13,400×g for 1 minute to pellet the microspheres and 20 seconds of sonication to resuspend the microspheres. Subsequently the microspheres were suspended in 500 μL of a 16 mg/mL solution of cysteamine and 30 mg/mL solution of EDC in 0.01% Tween20, 0.1 M MES buffer, pH 6.0 and placed on a rotating mixer protected from light for 2 hours. The microspheres were washed three times with 500 μL of water and three times with 500 μL of 0.1 M sodium chloride/0.1 M sodium acetate buffer, pH 4.5. The disulfide bonds of the bound cysteamine groups were reduced by suspending the microspheres in 500 μL of a 11 mg/mL solution of dithiothreitol (DTT) in 0.1 M sodium acetate/0.1 M sodium chloride buffer, pH 4.5. The microspheres were placed on a rotating mixer for 30 minutes and afterwards washed three times with 500 μL of methanol. Then they were suspended in 500 μL of dichloromethane and 5 μL of vinyl sulfone (VS) was added. After mixing on a rotating mixer for 14 hours, 500 μL of methanol was added and the microspheres were recovered and washed three times with 500 mL of methanol. The microspheres were suspended and stored in 1 mL of methanol. The just described procedure is graphically described in Entry 5b of Table 1.

7.0.6 Protected Vinyl Sulfone

The following describes a method for the preparation of an activated surface capable of immobilizing a biomolecule in accordance with the present invention. In particular, the following example describes a method for converting the activated polystyrene microspheres of the previous example into a more hydrolysis resistant form.

Microspheres prepared according to Example 5.0.5 were suspended in 800 μL of a solution containing 3 mg of sodium thiosulfite, 0.01% Tween 20, and sodium phosphate buffer, pH 4.0 for 14 hours. The microspheres were washed three times with 500 µL of DI water. The microspheres were suspended and stored in 1 mL of DI water. The microspheres are not reactive with nucleophiles unless they are first treated with a buffer of pH 9-10. The just described procedure is graphically described in Entry 5c of Table 1.

7.0.7 Tetra-Fluoro Sulfo-Phenyl Ester (TFS)

The following describes a method for the preparation of an activated surface capable of immobilizing a biomolecule in accordance with the present invention. In particular, the following example describes a method for directly activating carboxylated polystyrene microspheres with tetra-fluoro sulfophenyl esters.

300 µL (32 million microspheres) of a carboxylated polystyrene microsphere solution (5.5 µm) was washed three times with 500 µL of a solution containing 0.01% Tween20 and 0.1 M MES buffer, pH 6.0 using centrifugation at 13,400×g for 1 minute to pellet and 20 seconds of sonication to resuspend the microspheres. Then they were suspended in 500 µL of a solution containing 24 mg/mL of 2,3,5,6 tetrafluorophenol-4-sulfate (synthesized from 2,3,5,6 tetrafluorophenol according to the procedure of Gee, K. R. et al., *Tetrahedron Lett.*, 1999, 40, 1472-1474), 220 mg/mL of EDC, 0.01% Tween20, and 0.1 M MES buffer, pH 6.0 and then placed on a rotating mixer protected from light for 2 hours. The microspheres were washed three times with 500 µL of DI water. The microspheres were suspended and stored in 1 mL of DI water. The just described procedure is graphically described in Entry 6 of Table 1.

7.1 Examples of Novel Reactive Group Evaluation

In order to quantify the reactivity of the different novel reactive functional groups on polystyrene microspheres, a simple assay was developed using a biotin-amine derivative. First, biotin-LC-PEO-amine (obtained from Pierce, Rockford, Ill.) was coupled to carboxylated microspheres using typical EDC-mediated methods, followed by reaction with streptavidin-PE. The optimum concentrations of both biotin-amine and streptavidin-PE (obtained from Molecular Probes, Eugene, Oreg.) were titrated. This coupling assay provided a "standard" by which to measure and compare the reactivity of microspheres modified with the novel reactive functional groups. The modified microspheres are evaluated by reacting the biotin-amine directly, followed by reaction with streptavidin-PE. Functional group stability was evaluated by storing the microspheres either in buffer (pH 6; 4° C.) or dry, and performing the biotin-LC-PEO-amine assay at set intervals (e.g., days, weeks, months, etc.).

According to our test results our new novel reactive groups exhibit very desirable properties. For example, novel reactive groups show good reactivity with nucleophilic compounds, have substantially improved stability in aqueous media, form stable conjugates, require no additional activating reagents (e.g., EDC and/or NHS esters), and may provide more specific conjugation (i.e., reduce non-specific interaction/binding with solid substrates) thus protecting the integrity of biomolecules.

7.1.1 Coupling Reactivity and Reproducibility

Figure 1:
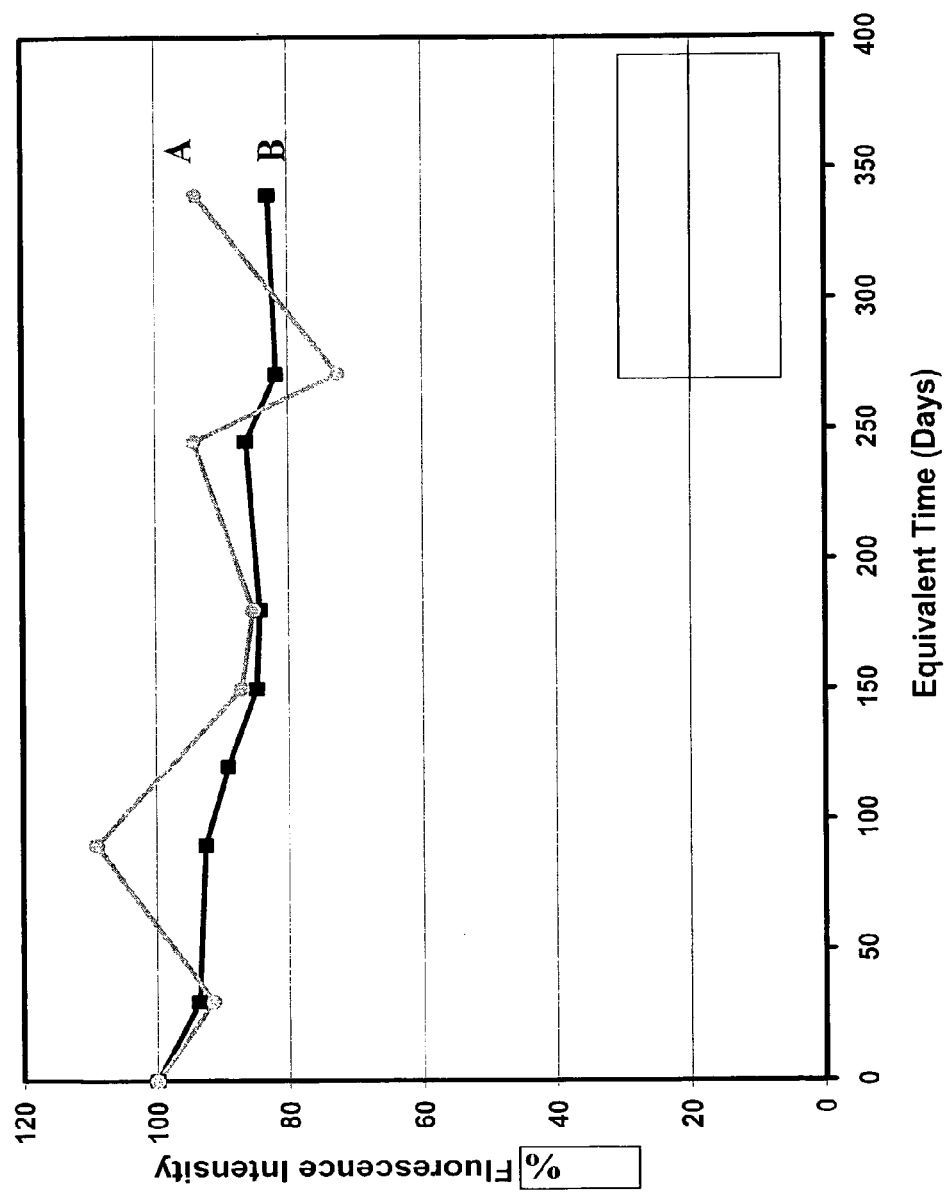
FIG. 1 shows a comparison of the COOH-functionalized microsphere, EDC coupling method (A) to mono-fluoro squaric acid-functionalized microspheres (MFS) (B) over time (accelerated at 25° C.). The novel pre-activated microspheres (B) provide more reproducible coupling day-to-day than the standard EDC-mediated reactions (A).

An accelerated stability study comparing the EDC-mediated coupling method to mono-fluoro squaric acid (MFS)-modified microspheres was carried out over an equivalent of 350 days. Using the biotin-amine model assay, results showed comparable reactivity between the two methods. Results also show the mono-fluoro squaric acid (MFS)-modified microspheres provide more reproducible coupling day-to-day. As depicted in FIG. 1, the EDC coupling method showed 20% changes in coupling throughout the entire experiment. During the equivalent 350 days, the mono-fluoro squaric acid (MFS)-modified microspheres lost some activity gradually, retaining 80% activity at the end of the study (i.e., the greatest change in activity was shown at the end of 350 equivalent days). Improvements in storage procedures are expected to eliminate any loss of activity for modified microspheres.

7.1.2 Stability

Figure 2:
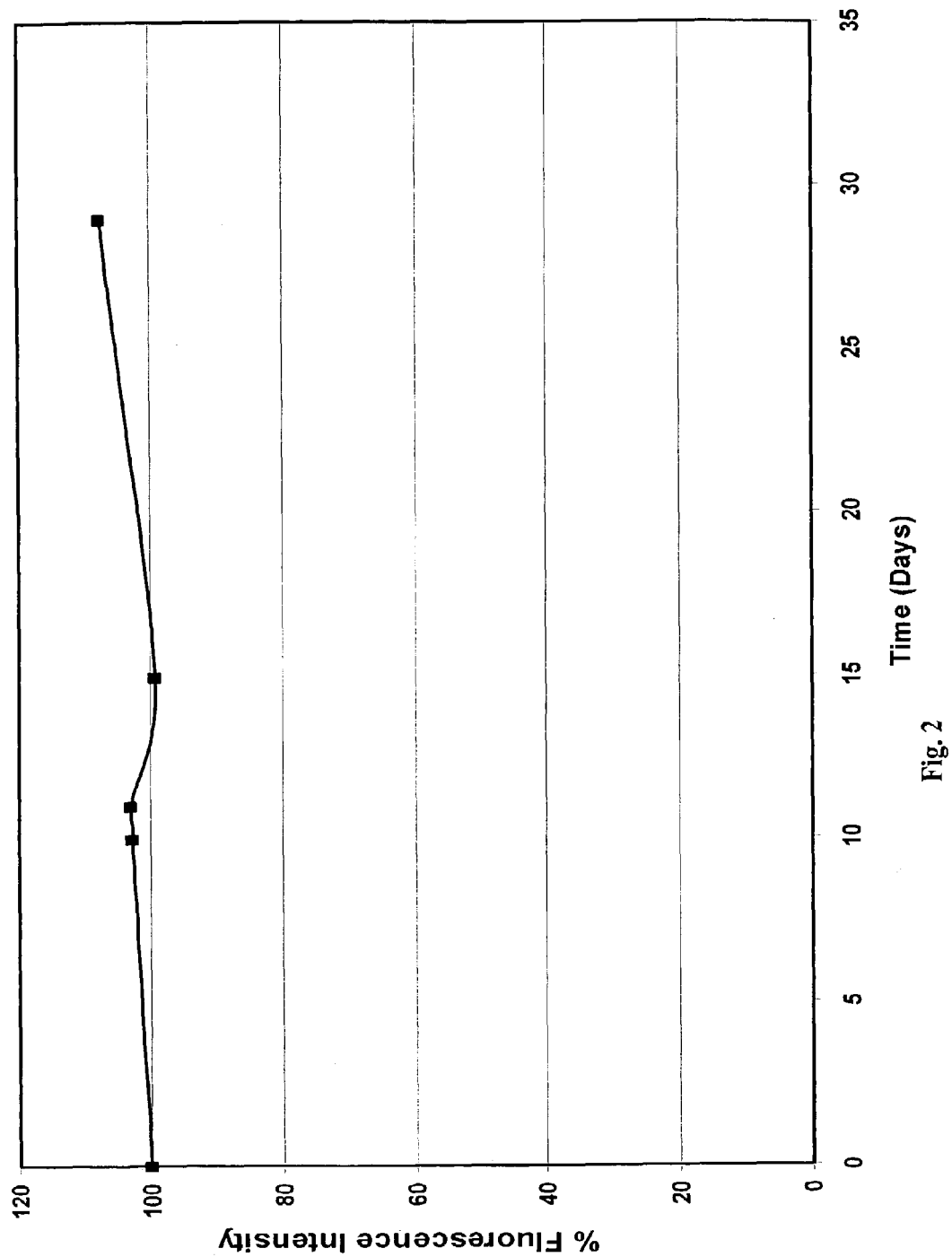
FIG. 2 shows a stability study of vinyl sulfone (VS)-functionalized microspheres stored in buffer, pH 6 at 4° C.
Figure 3:
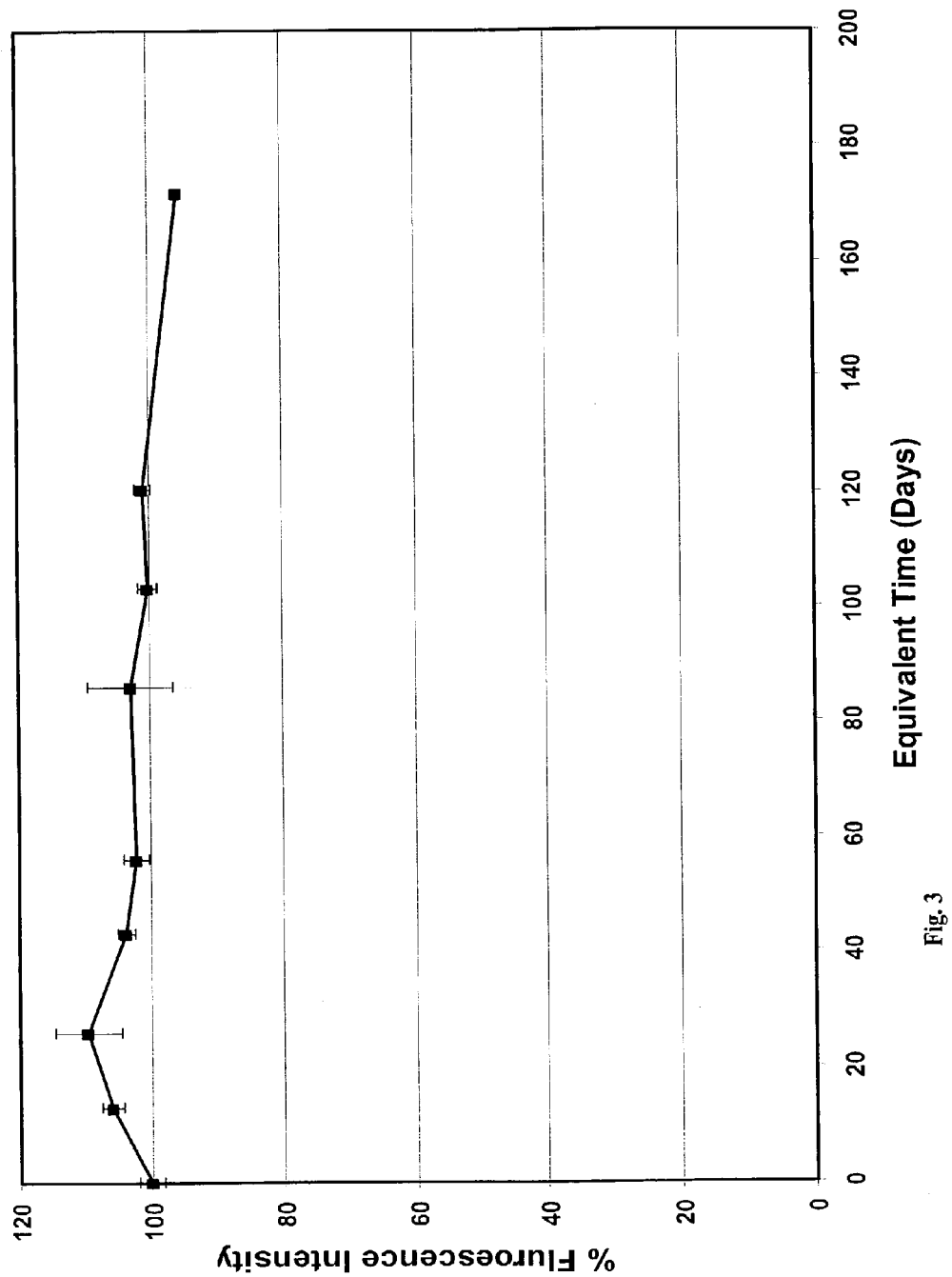
FIG. 3 shows an accelerated stability study of mono-fluoro squaric acid (MFS)-functionalized microspheres stored dry.
Figure 4:
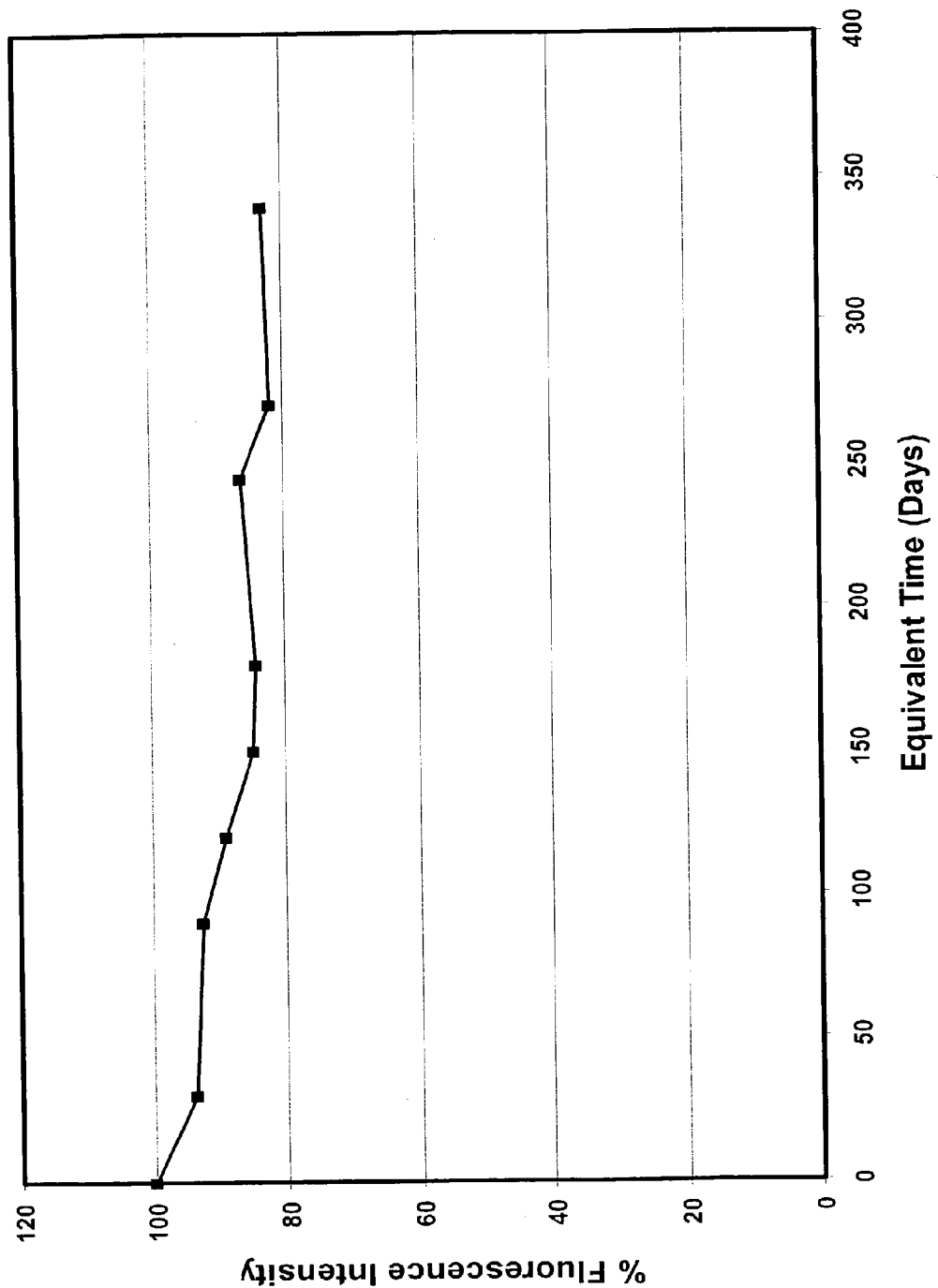
FIG. 4 shows an accelerated stability study of mono-fluoro squaric acid (MFS)-functionalized microspheres stored dry over a longer time period than shown in FIG. 3.
Figure 5:
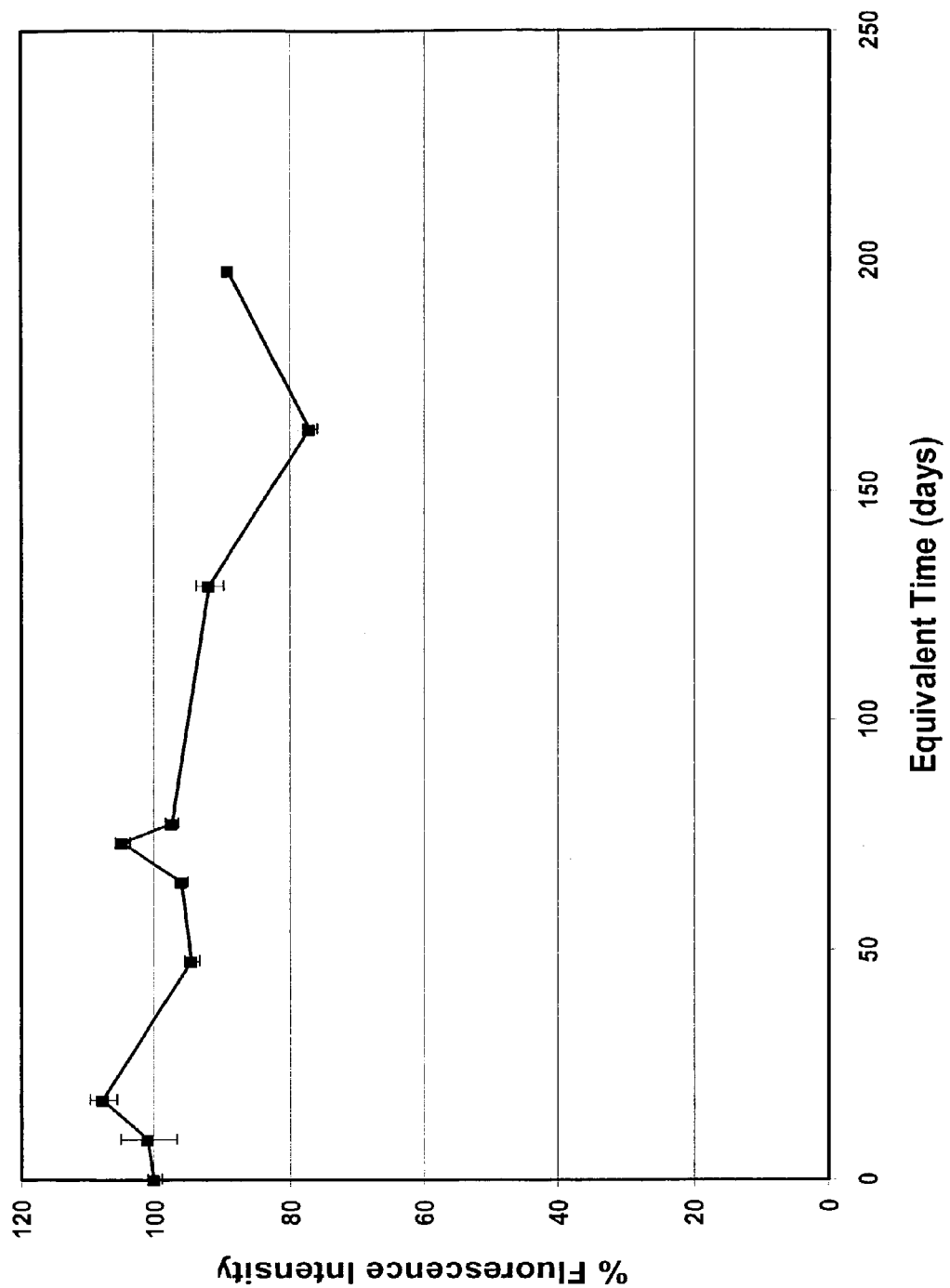
FIG. 5 shows an accelerated stability study of tetra-fluoro-sulfopheyl ester (TFS)-functionalized microspheres stored dry.
Figure 6:
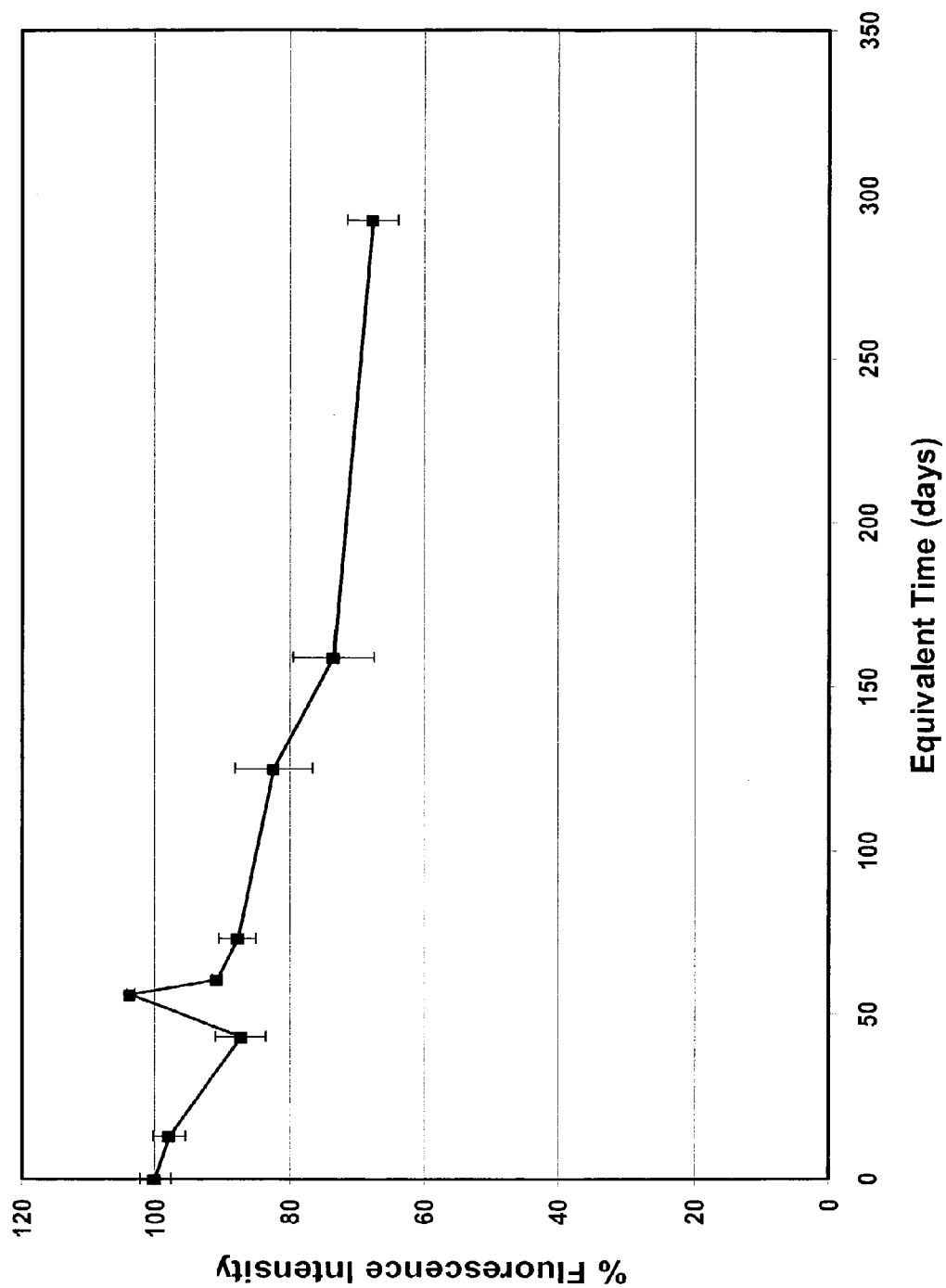
FIG. 6 shows an accelerated stability study of vinyl sulfone (VS)-functionalized microspheres stored dry.

Results show that microspheres modified with novel reactive groups have substantially improved stability in aqueous media. FIG. 2 depicts an example of the stability of vinyl-sulfone (VS)-functionalized microspheres in buffer for at least 30 days. This is a substantial improvement compared to EDC and NHS reagents, however, since there is a trade-off between reactivity and stability, we have also evaluated various drying and storage methods for long-term storage (including for example, 6 months, ≧approximately 6 months, greater than six months, six months to nine months, six months to one year, six months to two years, etc.) of the modified microspheres. FIGS. 3-6 depict examples of dry storage condition stability studies. Storage vessels that provide superior moisture barrier properties to those used in this study, will prevent loss of activity over time.

7.1.3 Bioassays

The performance of modified microspheres in real assays compared to the COOH microsphere-EDC method was evaluated. FIG. 7 shows a coupling titration of an amino-modified DNA probe on COOH-functionalized microspheres (EDC-mediated reaction) vs. pre-activated microsphere method. Both coupling titrations were performed at 25° C. The DNA compliment target concentration for the assay was 20 fmoles at a hybridization temperature of 55° C. Results show the COOH-EDC method yields a non-linear response to the amount of probe coupled to the microsphere. The pre-activated microsphere probe titration is more linear, suggesting a more specific coupling of the probe. Both results are reproducible. Note: 25° C. is not an optimal coupling temperature for the pre-activated microspheres. The signal is expected to improve with optimization of coupling temperature, as well as other parameters.

7.2 Examples of Coupling Procedures

7.2.1 Biotin-LC-PEO Amine

Surface-modified microspheres were washed three times with phosphate buffer (pH 6, 100 mM) and counted. $2.5 \times 10^7$ microspheres were aliquoted and washed once with phosphate buffer (pH 8, 100 mM). A solution of PEO-LC-biotin-amine (17.4 mg/mL) was prepared in phosphate buffer (pH 8, 100 mM). 100 µL of this solution was added to the microspheres, in 900 µL phosphate buffer (pH 8, 100 mM). The suspension was incubated at 37° C. for 1 hour. After the reaction was complete, the microspheres were washed three times with PBS-TBN (phosphate buffered saline, pH 7.4 with 0.02% Tween20 and 1 g/L bovine serum albumin), and recounted. A suspension of 100,000 microspheres/mL PBS-TBN was reacted with 1 µg Streptavidin-PE for 1 hour at room temperature. Subsequently the microspheres were washed three times and resuspended in 1 mL PBS-TBN. The fluorescence intensity of the microspheres was analyzed on a Luminex 100™ instrument.

7.2.2 Biotinylated IgG

A suspension of $25 \times 10^6$ surface-modified microspheres was washed with 1 mL carbonate buffer (pH 9, 100 mM). A 1 mL solution of IgG (50 µg/mL in 0.1 M pH 9 carbonate buffer) was added to the microspheres, vortexed, sonicated and incubated at 37° C. for 1 hour. After 1 hour, the sample was washed with 1 mL PBS-TBN (phosphate buffered saline, pH 7.4 with 0.02% Tween20 and 1 g/L bovine serum albumin). A suspension of 100,000 microspheres/mL PBS-TBN was reacted with 1 µg Streptavidin-PE for 1 hour at room temperature. Subsequently the microspheres were washed three times and resuspended in 1 mL PBS-TBN. The fluorescence intensity of the microspheres was analyzed on a Luminex 100™ instrument.

7.2.3 Biotinylated Oligonucleotides $5 \times 10^6$ surface-modified microspheres were dispensed into a 1.5 ml centrifuge tube and washed with 1 mL of carbonate buffer (pH 9, 100 mM). 50 µL carbonate buffer (pH 9, 100 mM) was added to the microspheres. 1 µL of a 1 mM solution of amino-modified oligonucleotide was added and the suspension was incubated at 37° C. for 1 hour. After 1 hour the sample was washed with PBS-TBN. A suspension of 100,000 microspheres/mL PBS-TBN was reacted with 1 µg Streptavidin-PE for 1 hour at room temperature. Subsequently the microspheres were washed three times and resuspended in 1 mL PBS-TBN. The fluorescence intensity of the microspheres was analyzed on a Luminex 100™ instrument.

Those skilled in the art will recognize, or be able to ascertain using no more than routine experimentation, many equivalents to the specific embodiments of the invention described herein. Such equivalents are intended to be encompassed by the following claims.

TABLE 1

Summary of Functional Groups and Synthetic Routes to FunctionalizedMicrospheres

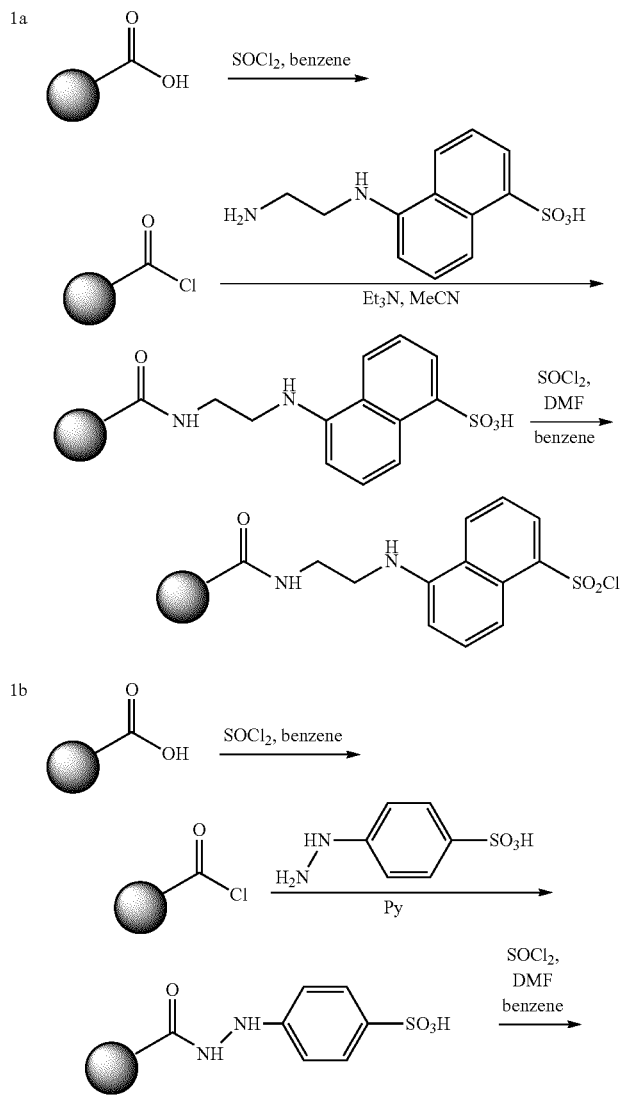

TABLE 1-continued
Summary of Functional Groups and Synthetic Routes to Functionalized Microspheres
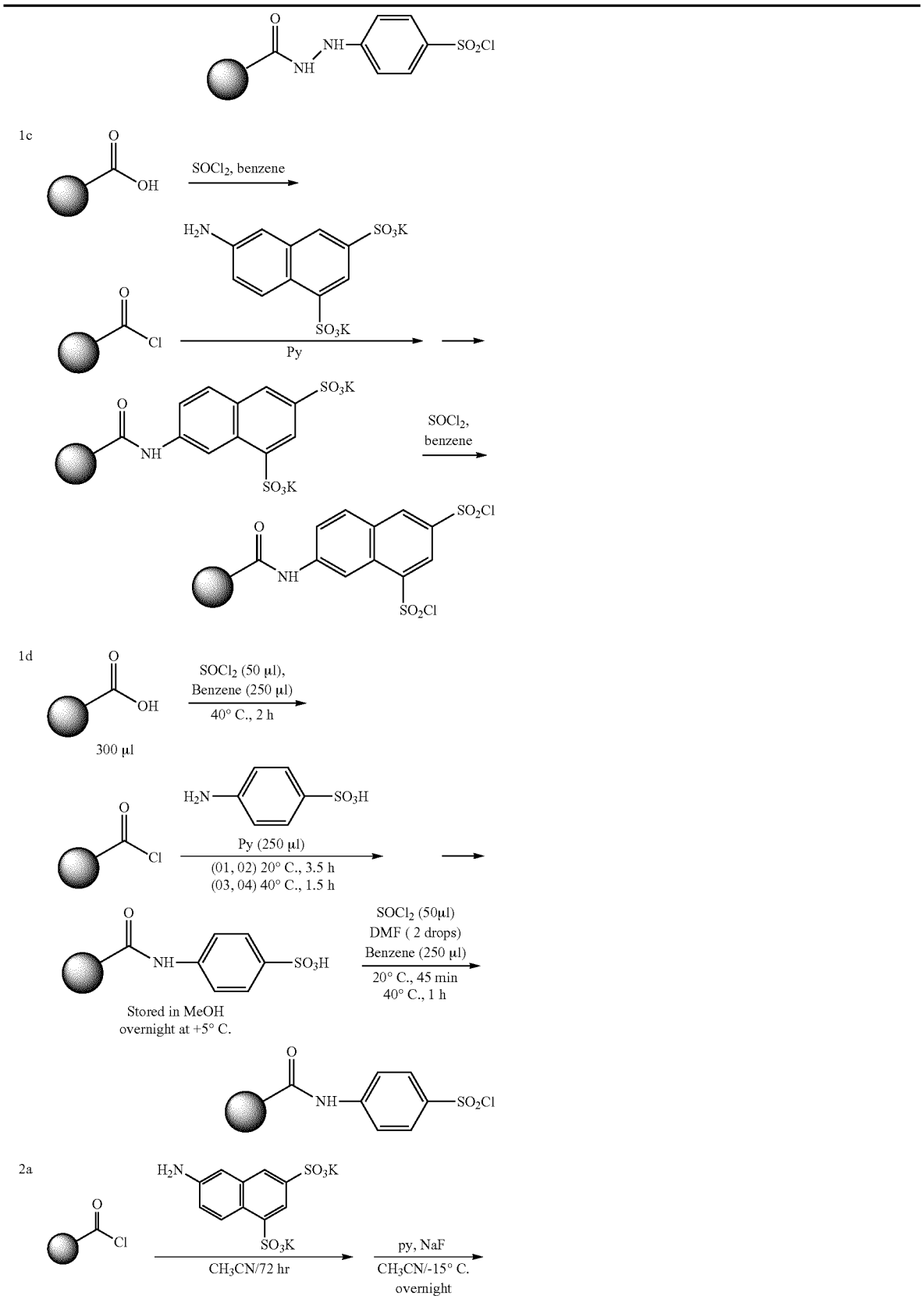

TABLE 1-continued
Summary of Functional Groups and Synthetic Routes to Functionalized Microspheres
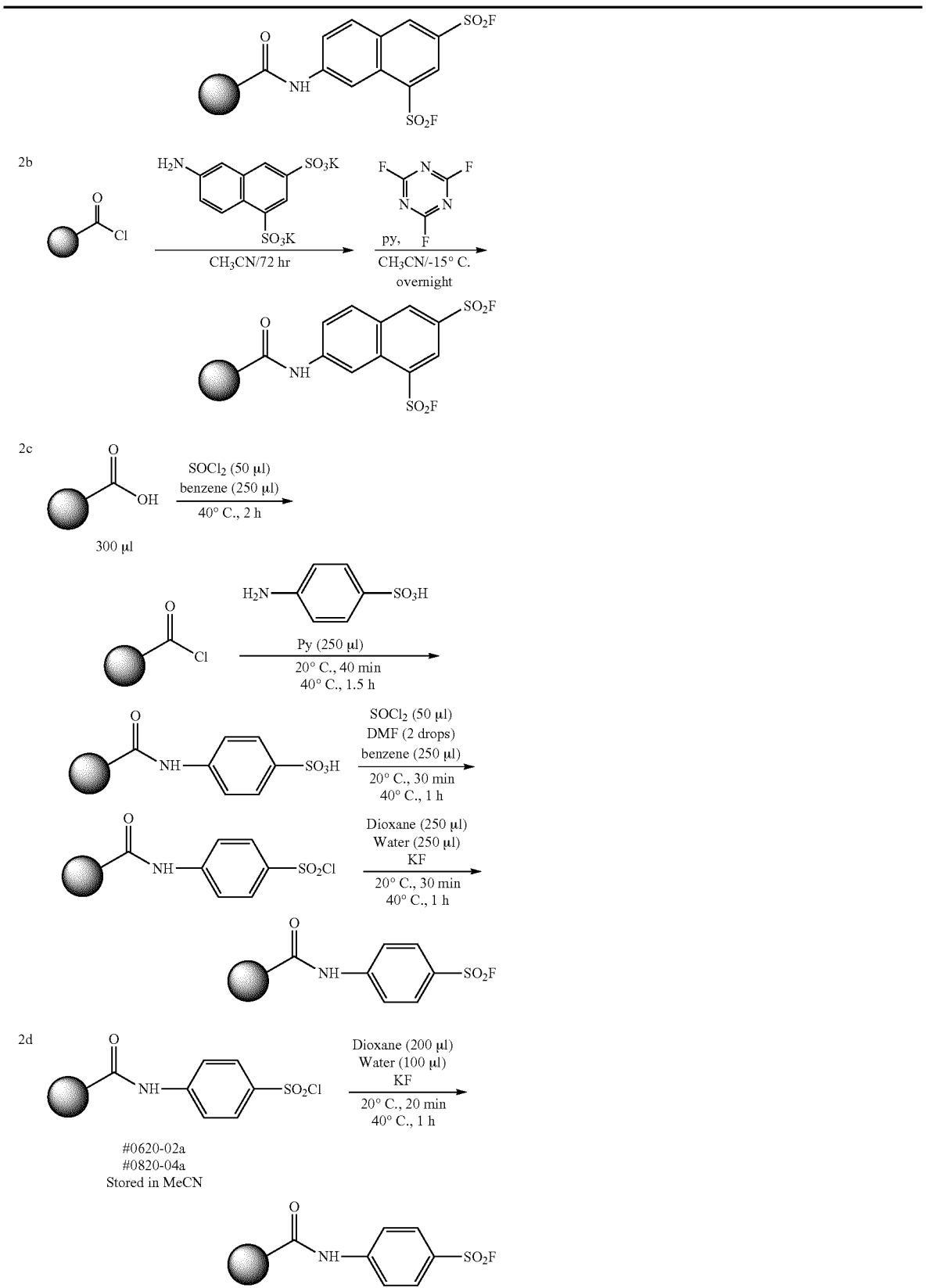

TABLE 1-continued
Summary of Functional Groups and Synthetic Routes to FunctionalizedMicrospheres
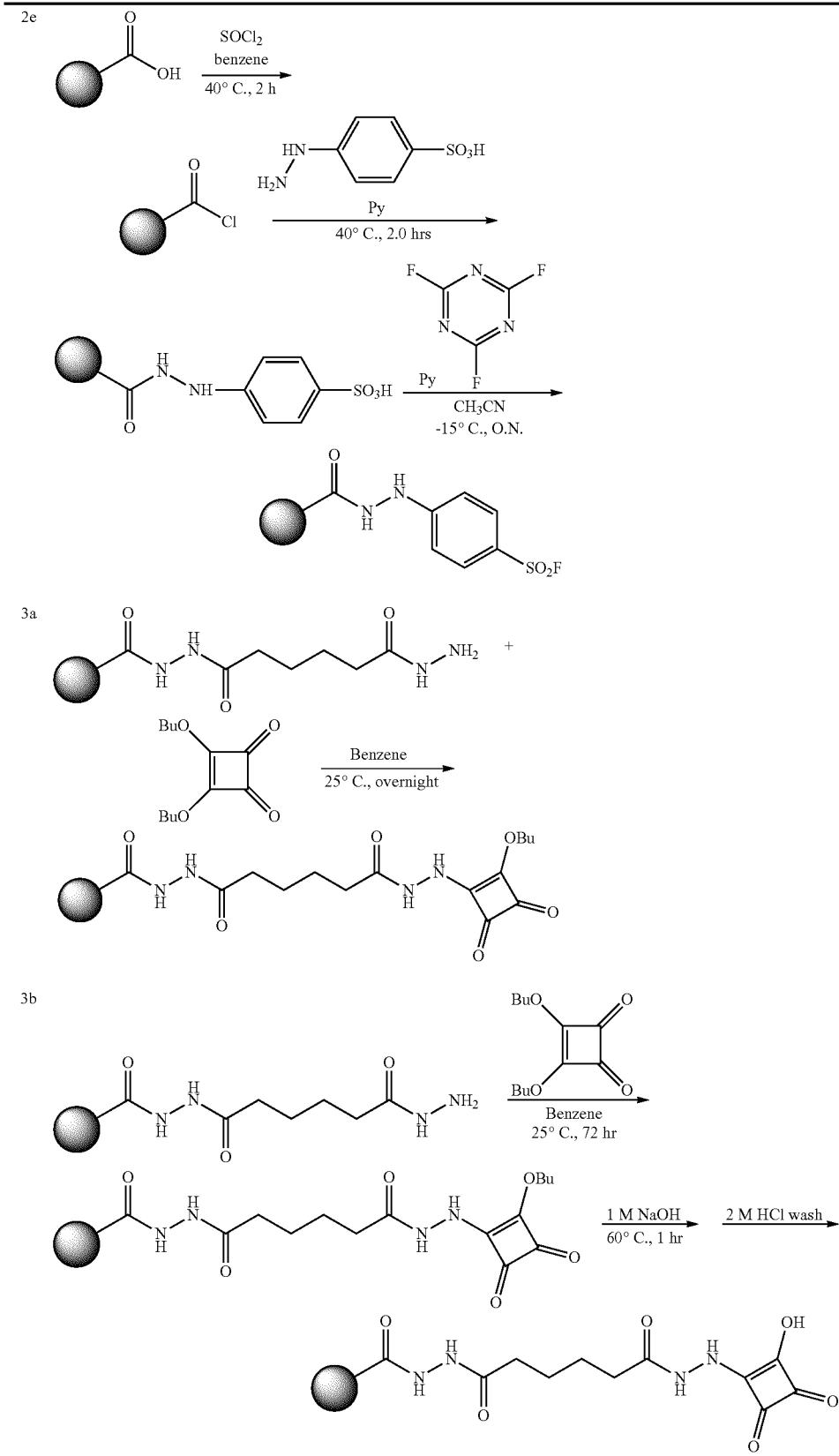

TABLE 1-continued
Summary of Functional Groups and Synthetic Routes to FunctionalizedMicrospheres
3c
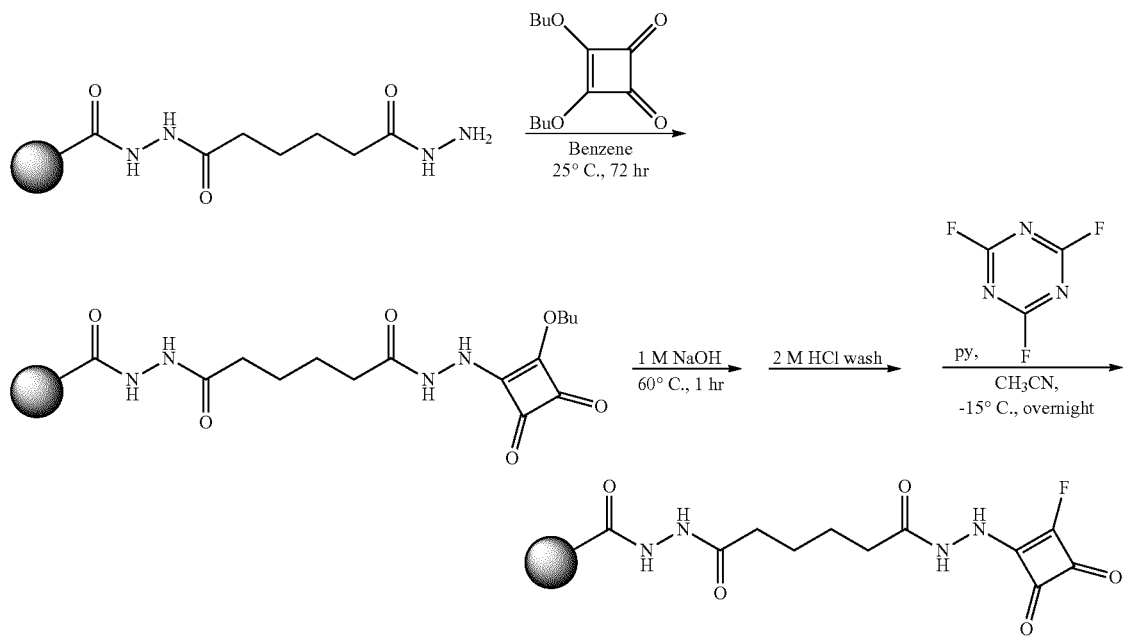
3d
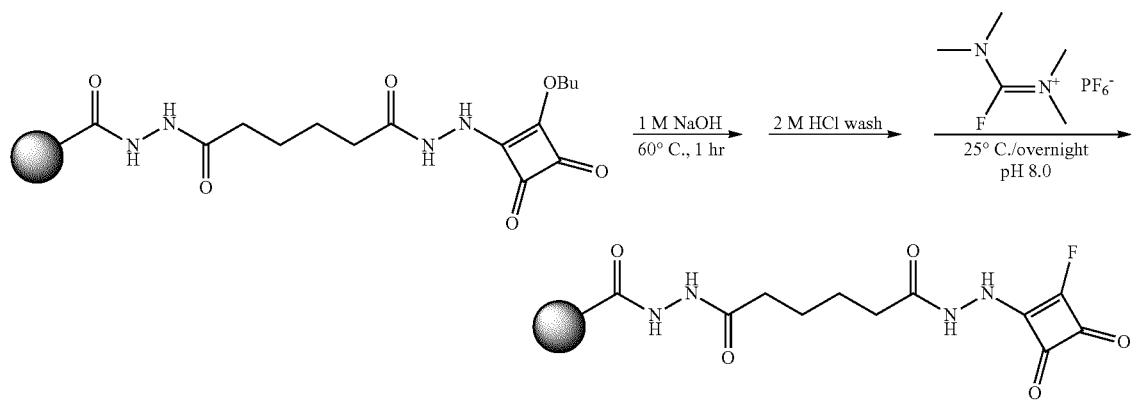
3e
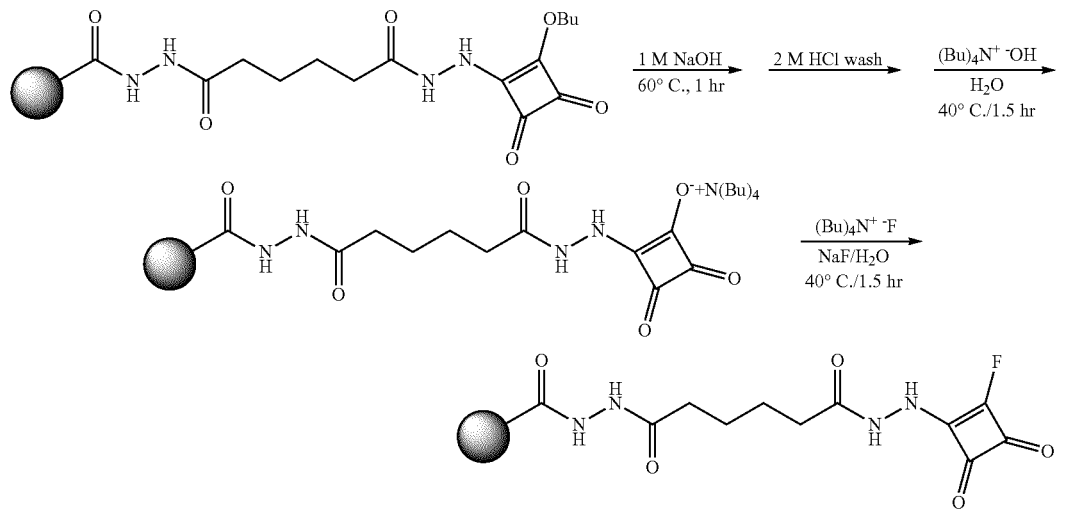

TABLE 1-continued
Summary of Functional Groups and Synthetic Routes to FunctionalizedMicrospheres
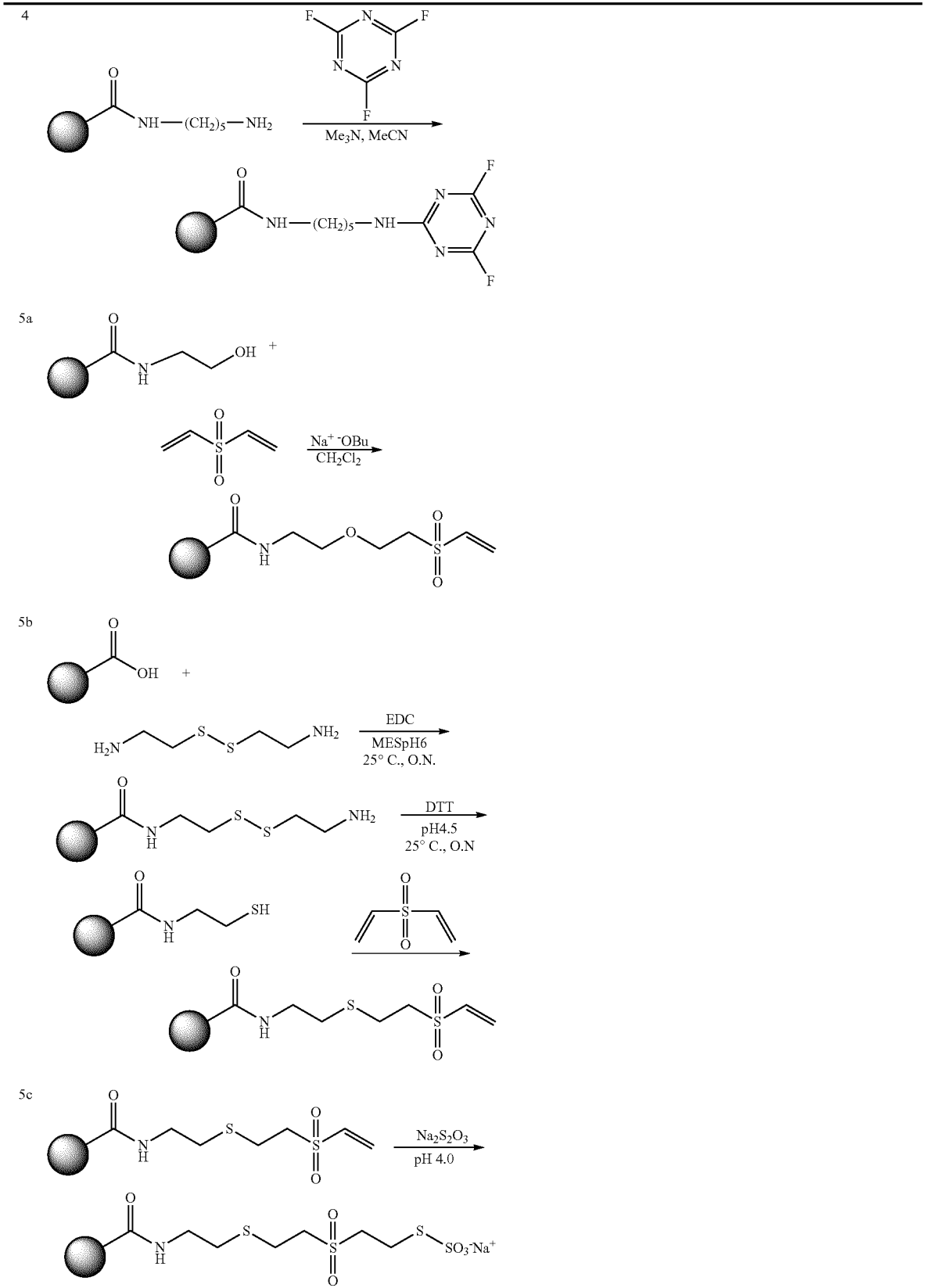

TABLE 1-continued

Summary of Functional Groups and Synthetic Routes to FunctionalizedMicrospheres

6 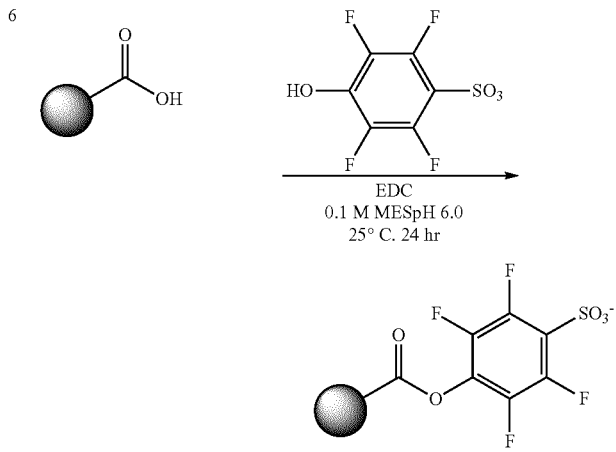

TABLE 2

Summary of Representative Linker Groups $R_n$

1. —X—CH$_2$CH$_2$—(O—CH$_2$)$_m$)$_n$—X— X = NH, S, O, Si, C(=O)

n = 0-500, m = 0-5

2. —E$_1$—(CF$_2$)—(O—(CF$_2$)$_m$)$_n$—E$_2$— E$_1$, E$_2$ = NH, S, O, Si, C(=O)

n = 0-500, m = 0-5

3. —E$_1$—(CH$_2$CH$_2$)—N[(CH$_2$)$_2$O(CH$_2$)$_2$E$_2$—][(CH$_2$)$_2$O(CH$_2$)$_2$E$_3$—]

E1, E2, E3, = NH, S, O, Si, C(=O), PO$_4$

4. —E$_1$—(CH$_2$)$_n$—E$_2$— E$_1$, E$_2$ = NH, S, O, Si, C(=O) n = 0-25

5. —E$_1$—CH$_2$CH$_2$—NH—(CH$_2$)$_m$)$_n$—E$_2$—

E$_1$, E$_2$ = NH, S, O, Si, C(=O) n = 0-500, m = 0-5

6. —HNHN—S(=O)$_2$—NHNH—

TABLE 2-continued
Summary of Representative Linker Groups $R_n$
7 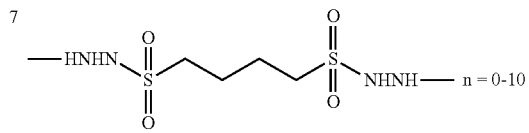 n = 0-10
8 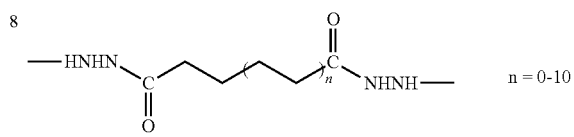 n = 0-10
9 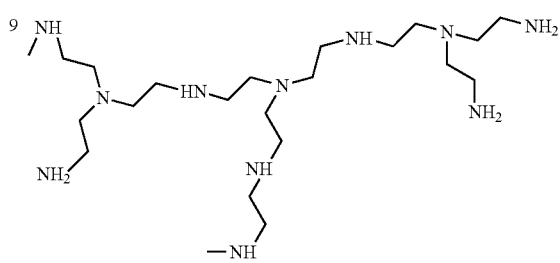
10 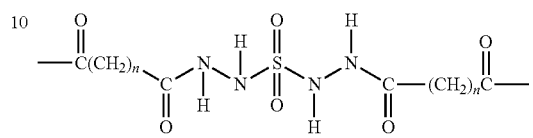
n = 0-10
11 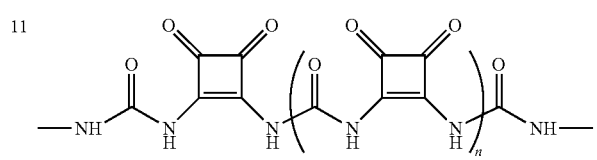
n = 0-5
12 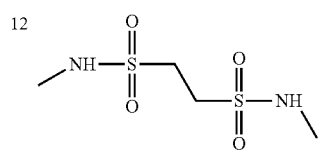
n = 1-5
13 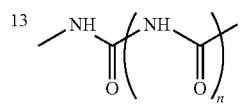
n = 0-6

TABLE 2-continued

Summary of Representative Linker Groups $R_n$

14 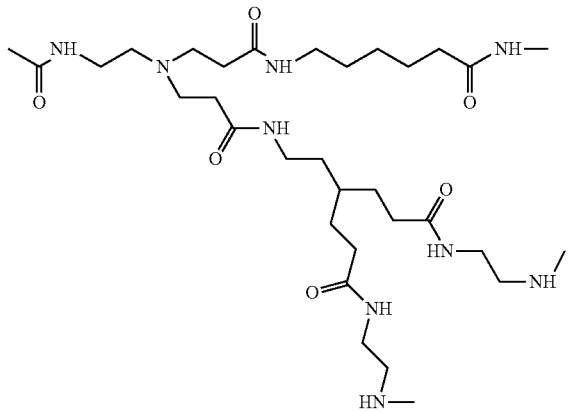 and other amino terminated dendritic structures

15 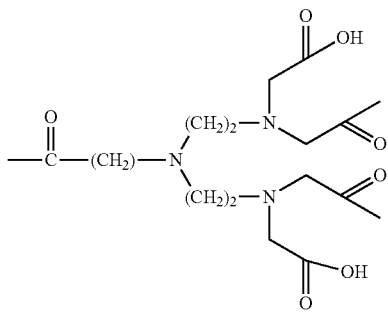 and other carboxyl terminated dendritic structures

16 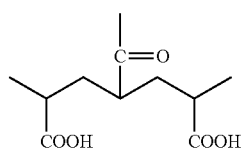

n = 0-20

17 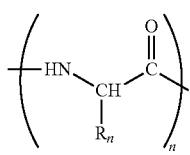

n = 1 – 30
$R_n$ = groups needed to form various natural and unnatural amino acids

What is claimed is:

1. A method for coupling two or more entities together, comprising:

(a) providing one or more conjugate compositions each having one or more of Structures 1-6 in any combination:

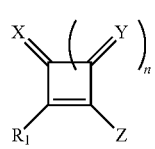

1

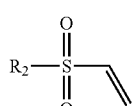

2

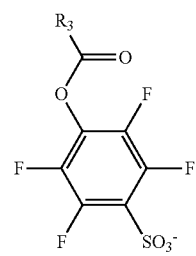

3

-continued

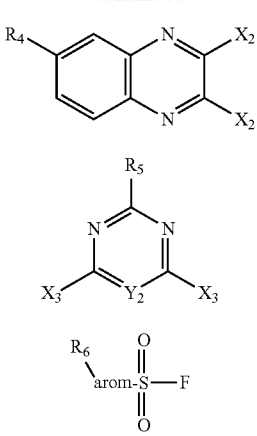

wherein:

n is 0, 1, 2, or 3;

X and Y are oxygen and/or sulfur in any combination;

$X_2$ and $X_3$ are chlorine or fluorine;

$Y_2$ is nitrogen or carbon;

arom is a substituted or unsubstituted phenyl, naphthyl or other polycyclic aromatic ring structure;

Z is chloride, fluoride, 2,3,5,6-tetrafluoro-4-sulfo-phenoxide, N-hydroxysuccinimide, or other electrophilic group; and $R_1$-$R_6$ comprise hydrocarbon linker groups containing from 2-1000 atoms, optionally containing one or more halogen or heteroatoms selected from the group consisting of O, N, Si, P and S;

wherein said one or more of Structures 1-6 of the one or more conjugate compositions are connected through their respective linker groups, $R_1$-$R_6$, to at least one polymeric micro- or nano-particle having polystyrene/divinyl benzene and carboxyl functional groups at least on its surface;

(b) providing one or more nucleophile-containing entities comprised of:
a 2-D film or substrate;
a micro- or nano-particle of any size or shape composed of organic polymer, MIPS, glass, metal, clay, resin, diatomaceous earth, zeolite, inorganic crystal, semiconductor particle, semiconductor nanocrystal, magnetic particle, fullerene, nanotube or any combination thereof; or
an enzyme, antibody, protein, DNA, RNA, nucleotide, PNA, carbohydrate, fatty acid, lectin, peptide, receptor, chromophore, fluorophore, bio- or chemi-luminescent compound, J or H aggregate, cell, bacteria, virus, whole prokaryotic or eukaryotic organism, synthetic or natural membrane, biotin, hapten, organic monomer or polymer, or dendrimer, or any combination thereof; and (c) reacting said one or more conjugate compositions with said one or more nucleophile-containing entities to link said one or more nucleophile-containing entities to the at least one polymeric micro- or nano-particle by way of said one or more linker groups of Structures 1-6.

2. The method of claim 1, wherein the step of reacting said one or more conjugate compositions with said one or more nucleophile-containing entities comprises crosslinking said one or more nucleophile-containing entities to the at least one polymeric micro- or nano-particle by way of said one or more linker groups of Structures 1-6.

3. The method of claim 1, wherein at least one of the one or more conjugate compositions comprises Structure 1, and wherein $R_1$ is chloride, fluoride, 2,3,5,6-tetrafluoro-4-sulfo-phenoxide, N-hydroxysuccinimide or other electrophilic group.

4. The method of claim 1, wherein at least one of the one or more conjugate compositions comprises Structure 1, and wherein Z for Structure 1 is fluoride.

5. The method of claim 1, further comprising:
(d) providing one or more bridge group compositions each having one or more of Structures 1-6, in any combination, conjugated by their respective linker groups $R_1$-$R_6$ to one or more nucleophilic groups, wherein if two or more of Structures 1-6 are joined together within the one or more bridge group compositions, they are joined together through their respective linker groups $R_1$-$R_6$, wherein said joining is one or more of end-to-end, branched, or dendritic, in any combination; and
(e) reacting said one or more bridge group compositions with said one or more nucleophile-containing entities and one or more conjugated compositions produce at least two crosslinked entities.

* * * * *